(12) United States Patent
Marsh et al.

(10) Patent No.: US 8,664,176 B2
(45) Date of Patent: Mar. 4, 2014

(54) TREATMENT FOR AGE-RELATED MACULAR DEGENERATION AND OTHER DISEASES OF THE EYE

(75) Inventors: Henry C. Marsh, Reading, MA (US); Lawrence Thomas, Easton, MA (US); Hua Gao, Farmington Hills, MI (US); Xiaoxi Qiao, Farmington Hills, MI (US)

(73) Assignee: Celldex Therapeutics, Inc., Needham, MA (US)

( * ) Notice: Subject to any disclaimer, the term of this patent is extended or adjusted under 35 U.S.C. 154(b) by 783 days.

(21) Appl. No.: 12/311,962

(22) PCT Filed: Oct. 19, 2007

(86) PCT No.: PCT/US2007/022276
§ 371 (c)(1),
(2), (4) Date: Feb. 4, 2010

(87) PCT Pub. No.: WO2008/048675
PCT Pub. Date: Apr. 24, 2008

(65) Prior Publication Data
US 2010/0130413 A1    May 27, 2010

Related U.S. Application Data

(60) Provisional application No. 60/853,201, filed on Oct. 20, 2006, provisional application No. 60/928,046, filed on May 7, 2007.

(51) Int. Cl.
*A61K 38/00* (2006.01)

(52) U.S. Cl.
USPC ............................................. 514/1.1

(58) Field of Classification Search
None
See application file for complete search history.

(56) References Cited

U.S. PATENT DOCUMENTS

| | | | |
|---|---|---|---|
| 5,456,909 A | 10/1995 | Marsh, Jr. et al. | |
| 5,981,481 A | 11/1999 | Fearon et al. | |
| 6,193,979 B1 | 2/2001 | Rittershaus et al. | |
| 6,458,360 B1 | 10/2002 | Fearon et al. | |
| 6,713,606 B1 | 3/2004 | Smith et al. | |
| 2006/0067935 A1 | 3/2006 | Ambati | |
| 2007/0238654 A1* | 10/2007 | Deschatelets et al. | 514/9 |
| 2012/0004393 A1* | 1/2012 | Lambris et al. | 530/324 |

FOREIGN PATENT DOCUMENTS

| | | |
|---|---|---|
| WO | WO 2006/042252 A2 | 4/2006 |
| WO | WO 2006/042329 A2 | 4/2006 |
| WO | WO 2007/044668 A2 | 4/2007 |
| WO | WO 2007/149567 A2 | 12/2007 |

OTHER PUBLICATIONS

Weisman et al., "Soluble Human Complement Receptor Type I: In Vivo Inhibitor of Complement Suppressing Post Ischemic Myocardial Inflammation and Necrosis", Science, 249: 146-151 (1990).

Barnum, S.R., "Inhibition of Complement as a Therapeutic Approach in Inflammatory Central Nervous System Disease", Mol. Med., 5: 569-582 (1999).

Edwards et al., "Complement Factor H Polymorphism and Age-Related Macular Degeneration", Science, 308: 421-424 (2005).

Hageman et al., "A common haplotype in the complement regulatory gene factor H (HF1/CFH) predisposes individuals to age-related macular degeneration", PNAS, 102(20): 7227-7232 (2005).

Haines et al., "Complement Factor H Variant Increases the Risk of Age-Related Macular Degeneration", Science, 308: 419-421 (2005).

Klein et al., "Complement Factor H Polymorphism in Age-Related Macular Degeneration", Science, 308: 385-389 (2005).

* cited by examiner

*Primary Examiner* — Robert Landsman
(74) *Attorney, Agent, or Firm* — Leon R. Yankwich; David G. O'Brien; Yankwich & Associates, P.C.

(57) ABSTRACT

A method is disclosed for treating diseases or disorders of the eye involving undesired neovascularization by administration of a complement inhibitory protein such as soluble complement receptor type I (sCR1). The present invention relates to the direct treatment of macular degeneration, particularly age-related macular degeneration (AMD), by administering a complement inhibitory protein intraocularly or systemically.

13 Claims, 3 Drawing Sheets

Negative Control      sCR1

SEQUENCE LISTING

<160> NUMBER OF SEQ ID NOS: 3

<210> SEQ ID NO 1
<211> LENGTH: 6117
<212> TYPE: DNA
<213> ORGANISM: Homo sapiens

<400> SEQUENCE: 1
atgggggcct cttctccaag aagcccggag cctgtcgggc cgccggcgcc cggtctcccc    60

```
ttctgctgcg gaggatccct gctggcggtt gtggtgctgc ttgcgctgcc ggtggcctgg      120
ggtcaatgca atgccccaga atggcttcca tttgccaggc ctaccaacct aactgatgag      180
tttgagtttc ccattgggac atatctgaac tatgaatgcc gccctggtta ttccggaaga      240
ccgtttctta tcatctgcct aaaaaactca gtctggactg tgctaagga caggtgcaga       300 cgtaaatcat gtcgtaatcc tccagatcct gtgaatggca tggtgcatgt gatcaaaggc      360
atccagttcg gatcccaaat taaatattct tgtactaaag gataccgact cattggttcc      420
tcgtctgcca catgcatcat ctcaggtgat actgtcattt gggataatga acacctatt       480 tgtgacagaa ttccttgtgg gctacccccc accatcacca atggagattt cattagcacc      540
aacagagaga attttcacta tggatcagtg gtgacctacc gctgcaatcc tggaagcgga      600
gggagaaagg tgtttgagct tgtgggtgag ccctccatat actgcaccag caatgacgat      660
caagtgggca tctggagcgg ccccgcccct cagtgcatta tacctaacaa atgcacgcct      720
ccaaatgtgg aaaatggaat attggtatct gacaacagaa gcttattttc cttaaatgaa      780
gttgtggagt ttaggtgtca gcctggcttt gtcatgaaag accccgccg tgtgaagtgc       840 caggccctga acaaatggga gccggagcta ccaagctgct ccagggtatg tcagccacct      900
ccagatgtcc tgcatgctga gcgtacccaa agggacaagg acaacttttc acctgggcag      960
gaagtgttct acagctgtga gcccggctac gacctcagag gggctgcgtc tatgcgctgc      1020 acccccagg gagactggag ccctgcagcc cccacatgtg aagtgaaatc ctgtgatgac       1080
ttcatgggcc aacttcttaa tggccgtgtg ctatttccag taaatctcca gcttggagca      1140
aaagtggatt ttgtttgtga tgaaggattt caattaaaag gcagctctgc tagttactgt      1200
gtcttggctg aatggaaag cctttggaat agcagtgttc cagtgtgtga acaaatcttt       1260
tgtccaagtc ctccagttat tcctaatggg agacacacag gaaaacctct ggaagtcttt     1320 cccttttggaa aagcagtaaa ttacacatgc gaccccacc cagacagagg gacgagcttc     1380
gacctcattg gagagagcac catccgctgc acaagtgacc ctcaagggaa tggggtttgg     1440
agcagccctg cccctcgctg tggaattctg ggtcactgtc aagccccaga tcattttctg      1500
tttgccaagt tgaaaacca aaccaatgca tctgactttc ccattgggac atctttaaag      1560
tacgaatgcc gtcctgagta ctacgggagg ccattctcta tcacatgtct agataacctg      1620
gtctggtcaa gtcccaaaga tgtctgtaaa cgtaaatcat gtaaaactcc tccagatcca     1680
gtgaatggca tggtgcatgt gatcacagac atccaggttg gatccagaat caactattct     1740
tgtactacag gcaccgact cattggtcac tcatctgctg aatgtatcct ctcgggcaat       1800 gctgccatt ggagcacgaa gccgccaatt gtcaacgaa ttccttgtgg gctacccccc         1860
accatcgcca atggagattt cattagcacc aacagagaga attttcacta tggatcagtg     1920
gtgacctacc gctgcaatcc tggaagcgga gggagaaagg tgtttgagct tgtgggtgag     1980
ccctccatat actgcaccag caatgacgat caagtgggca tctggagcgg ccccgccct      2040 cagtgcatta tacctaacaa atgcacgcct ccaaatgtgg aaaatggaat attggtatct     2100
gacaacagaa gcttattttc cttaaatgaa gttgtggagt ttaggtgtca gcctggcttt     2160
gtcatgaaag accccgccg tgtgaagtgc caggccctga acaaatggga gccggagcta      2220
ccaagctgct ccagggtatg tcagccacct ccagatgtcc tgcatgctga gcgtacccaa     2280
agggacaagg acaacttttc acccgggcag gaagtgttct acagctgtga gcccggctat     2340
gacctcagag gggctgcgtc tatgcgctgc acccccagg gagactggag ccctgcagcc      2400
cccacatgtg aagtgaaatc ctgtgatgac ttcatgggcc aacttcttaa tggccgtgtg     2460
```

-continued

```
ctatttccag taaatctcca gcttggagca aaagtggatt ttgtttgtga tgaaggattt    2520
caattaaaag gcagctctgc tagttattgt gtcttggctg aatggaaag  cctttggaat    2580 agcagtgttc cagtgtgtga acaaatcttt tgtccaagtc ctccagttat tcctaatggg    2640
agacacacag gaaaacctct ggaagtcttt ccctttggaa aagcagtaaa ttacacatgc    2700 gaccccacc  cagacagagg gacgagcttc gacctcattg gagagagcac catccgctgc    2760
acaagtgacc ctcaagggaa tggggtttgg agcagccctg cccctcgctg tggaattctg    2820
ggtcactgtc aagcccaga  tcattttctg tttgccaagt tgaaaaccca aaccaatgca    2880
tctgactttc ccattgggac atctttaaag tacgaatgcc gtcctgagta ctacgggagg    2940
ccattctcta tcacatgtct agataacctg gtctggtcaa gtcccaaaga tgtctgtaaa    3000
cgtaaatcat gtaaaactcc tccagatcca gtgaatggca tggtgcatgt gatcacagac    3060
atccaggttg gatccagaat caactattct tgtactacag ggcaccgact cattggtcac    3120
tcatctgctg aatgtatcct ctcaggcaat actgcccatt ggagcacgaa gccgccaatt    3180
tgtcaacgaa ttccttgtgg gctaccccca accatcgcca atggagattt cattagcacc    3240
aacagagaga ttttcactg  tggatcagtg gtgacctacc gctgcaatct ggaagcaga    3300 gggagaaagg tgtttgagct tgtgggtgag ccctccatat actgcaccag caatgacgat    3360
caagtgggca tctggagcgg ccccgcccct cagtgcatta tacctaacaa atgcacgcct    3420
ccaaatgtgg aaaatggaat attggtatct gacaacagaa gcttatttc  cttaaatgaa    3480 gttgtggagt ttaggtgtca gcctggcttt gtcatgaaag accccgccg  tgtgaagtgc    3540 caggccctga caaatggga  gccagagtta ccaagctgct ccagggtgtg tcagccgcct    3600
ccagaaatcc tgcatggtga gcataccca  agccatcagg acaactttc  acctgggcag    3660 gaagtgttct acagctgtga gcctggctat gacctcagag gggctgcgtc tctgcactgc    3720
acaccccagg gagactggag ccctgaagcc ccgagatgtg cagtgaaatc ctgtgatgac    3780
ttcttgggtc aactccctca tggccgtgtg ctatttccac ttaatctcca gcttgggca    3840 aaggtgtcct ttgtctgtga tgaagggttt cgcttaaagg gcagttccgt tagtcattgt    3900
gtcttggttg gaatgagaag cctttggaat aacagtgttc ctgtgtgtga acatatcttt    3960
tgtccaaatc ctccagctat ccttaatggg agacacacag gaactccctc tggagatatt    4020
ccctatggaa aagaaatatc ttacacatgt gaccccacc  cagacagagg gatgaccttc    4080
aacctcattg gggagagcac catccgctgc acaagtgacc tcatgggaa  tggggtttgg    4140 agcagccctg cccctcgctg tgaactttct gttcgtgctg gtcactgtaa aaccccagag    4200
cagtttccat ttgccagtcc tacgatccca attaatgact ttgagttcc  agtcgggaca    4260 tctttgaatt atgaatgccg tcctgggtat tttgggaaaa tgttctctat ctcctgccta    4320
gaaaacttgg tctggtcaag tgttgaagac aactgtagac gaaaatcatg tggacctcca    4380
ccagaaccct tcaatggaat ggtgcatata aacacagata cacagtttgg atcaacagtt    4440
aattattctt gtaatgaagg gtttcgactc attggttccc catctactac ttgtctcgtc    4500
tcaggcaata atgtcacatg ggataagaag gcacctattt tgtgagatcat atcttgtgag    4560 ccacctccaa ccatatccaa tggagacttc tacagcaaca atagaacatc ttttcacaat    4620 ggaacgtgg  taacttacca gtgccacact ggaccagatg gagaacagct gtttgagctt    4680
gtgggagaac ggtcaatata ttgcaccagc aaagatgatc aagttggtgt ttggagcagc    4740
cctccccctc ggtgtatttc tactaataaa tgcacagctc cagaagttga aaatgcaatt    4800
agagtaccag gaaacaggag tttcttttcc ctcactgaga tcatcagatt tagatgtcag    4860
```

-continued

```
cccgggtttg tcatggtagg gtcccacact gtgcagtgcc agaccaatgg cagatggggg    4920
cccaagctgc cacactgctc cagggtgtgt cagccgcctc cagaaatcct gcatggtgag    4980
cataccctaa gccatcagga caacttttca cctgggcagg aagtgttcta cagctgtgag    5040
cccagctatg acctcagagg ggctgcgtct ctgcactgca cgccccaggg agactggagc    5100
cctgaagccc ctagatgtac agtgaaatcc tgtgatgact tcctgggcca actccctcat    5160
ggccgtgtgc tacttccact taatctccag cttggggcaa aggtgtcctt tgtttgcgat    5220
gaagggttcc gattaaaagg caggtctgct agtcattgtg tcttggctgg aatgaaagcc    5280
ctttggaata gcagtgttcc agtgtgtgaa caaatctttt gtccaaatcc tccagctatc    5340
cttaatggga gacacacagg aactcccttt ggagatattc cctatggaaa agaaatatct    5400
tacgcatgcg acacccaccc agacagaggg atgaccttca acctcattgg ggagagctcc    5460
atccgctgca caagtgaccc tcaagggaat ggggtttgga gcagccctgc ccctcgctgt    5520
gaactttctg ttcctgctgc ctgcccacat ccacccaaga tccaaaacgg cattacatt    5580 ggaggacacg tatctctata tcttcctggg atgacaatca gctacacttg tgaccccggc    5640
tacctgttag tgggaaaggg cttcattttc tgtacagacc agggaatctg gagccaattg    5700
gatcattatt gcaaagaagt aaattgtagc ttcccactgt ttatgaatgg aatctcgaag    5760
gagttagaaa tgaaaaaagt atatcactat ggagattatg tgactttgaa gtgtgaagat    5820
gggtatactc tggaaggcag tccctggagc cagtgccagg cggatgacag atgggaccct    5880
cctctggcca aatgtacctc tcgtgcacat gatgctctca tagttggcac tttatctggt    5940
acgatcttct ttatttact catcattttc ctctcttgga taattctaaa gcacagaaaa    6000
ggcaataatg cacatgaaaa ccctaaagaa gtggctatcc atttacattc tcaaggaggc    6060
agcagcgttc atccccgaac tctgcaaaca aatgaagaaa atagcagggt ccttcct      6117
```

<210> SEQ ID NO 2
<211> LENGTH: 1998
<212> TYPE: PRT
<213> ORGANISM: Homo sapiens
<220> FEATURE:
<221> NAME/KEY: MISC_FEATURE
<222> LOCATION: (1)..(1998)
<223> OTHER INFORMATION: Full Length Protein

<400> SEQUENCE: 2

```
Gln Cys Asn Ala Pro Glu Trp Leu Pro Phe Ala Arg Pro Thr Asn Leu
1               5                   10                  15

Thr Asp Glu Phe Glu Phe Pro Ile Gly Thr Tyr Leu Asn Tyr Glu Cys
            20                  25                  30

Arg Pro Gly Tyr Ser Gly Arg Pro Phe Ser Ile Ile Cys Leu Lys Asn
        35                  40                  45

Ser Val Trp Thr Gly Ala Lys Asp Arg Cys Arg Arg Lys Ser Cys Arg
    50                  55                  60

Asn Pro Pro Asp Pro Val Asn Gly Met Val His Val Ile Lys Gly Ile
65                  70                  75                  80

Gln Phe Gly Ser Gln Ile Lys Tyr Ser Cys Thr Lys Gly Tyr Arg Leu
            85                  90                  95

Ile Gly Ser Ser Ser Ala Thr Cys Ile Ile Ser Gly Asp Thr Val Ile
            100                 105                 110

Trp Asp Asn Glu Thr Pro Ile Cys Asp Arg Ile Pro Cys Gly Leu Pro
        115                 120                 125

Pro Thr Ile Thr Asn Gly Asp Phe Ile Ser Thr Asn Arg Glu Asn Phe
    130                 135                 140
```

```
His Tyr Gly Ser Val Val Thr Tyr Arg Cys Asn Pro Gly Ser Gly Gly
145                 150                 155                 160

Arg Lys Val Phe Glu Leu Val Gly Glu Pro Ser Ile Tyr Cys Thr Ser
                165                 170                 175

Asn Asp Asp Gln Val Gly Ile Trp Ser Gly Pro Ala Pro Gln Cys Ile
            180                 185                 190

Ile Pro Asn Lys Cys Thr Pro Pro Asn Val Glu Asn Gly Ile Leu Val
            195                 200                 205

Ser Asp Asn Arg Ser Leu Phe Ser Leu Asn Glu Val Val Glu Phe Arg
210                 215                 220

Cys Gln Pro Gly Phe Val Met Lys Gly Pro Arg Arg Val Lys Cys Gln
225                 230                 235                 240

Ala Leu Asn Lys Trp Glu Pro Glu Leu Pro Ser Cys Ser Arg Val Cys
                245                 250                 255

Gln Pro Pro Pro Asp Val Leu His Ala Glu Arg Thr Gln Arg Asp Lys
            260                 265                 270

Asp Asn Phe Ser Pro Gly Gln Glu Val Phe Tyr Ser Cys Glu Pro Gly
            275                 280                 285

Tyr Asp Leu Arg Gly Ala Ala Ser Met Arg Cys Thr Pro Gln Gly Asp
290                 295                 300

Trp Ser Pro Ala Ala Pro Thr Cys Glu Val Lys Ser Cys Asp Asp Phe
305                 310                 315                 320

Met Gly Gln Leu Leu Asn Gly Arg Val Leu Phe Pro Val Asn Leu Gln
                325                 330                 335

Leu Gly Ala Lys Val Asp Phe Val Cys Asp Glu Gly Phe Gln Leu Lys
            340                 345                 350

Gly Ser Ser Ala Ser Tyr Cys Val Leu Ala Gly Met Glu Ser Leu Trp
            355                 360                 365

Asn Ser Ser Val Pro Val Cys Glu Gln Ile Phe Cys Pro Ser Pro Pro
            370                 375                 380

Val Ile Pro Asn Gly Arg His Thr Gly Lys Pro Leu Glu Val Phe Pro
385                 390                 395                 400

Phe Gly Lys Ala Val Asn Tyr Thr Cys Asp Pro His Pro Asp Arg Gly
                405                 410                 415

Thr Ser Phe Asp Leu Ile Gly Glu Ser Thr Ile Arg Cys Thr Ser Asp
            420                 425                 430

Pro Gln Gly Asn Gly Val Trp Ser Ser Pro Ala Pro Arg Cys Gly Ile
            435                 440                 445

Leu Gly His Cys Gln Ala Pro Asp His Phe Leu Phe Ala Lys Leu Lys
450                 455                 460

Thr Gln Thr Asn Ala Ser Asp Phe Pro Ile Gly Thr Ser Leu Lys Tyr
465                 470                 475                 480

Glu Cys Arg Pro Glu Tyr Tyr Gly Arg Pro Phe Ser Ile Thr Cys Leu
                485                 490                 495

Asp Asn Leu Val Trp Ser Ser Pro Lys Asp Val Cys Lys Arg Lys Ser
            500                 505                 510

Cys Lys Thr Pro Pro Asp Pro Val Asn Gly Met Val His Val Ile Thr
            515                 520                 525

Asp Ile Gln Val Gly Ser Arg Ile Asn Tyr Ser Cys Thr Thr Gly His
            530                 535                 540

Arg Leu Ile Gly His Ser Ser Ala Glu Cys Ile Leu Ser Gly Asn Ala
545                 550                 555                 560

Ala His Trp Ser Thr Lys Pro Pro Ile Cys Gln Arg Ile Pro Cys Gly
```

-continued

```
              565                 570                 575
Leu Pro Pro Thr Ile Ala Asn Gly Asp Phe Ile Ser Thr Asn Arg Glu
            580                 585                 590

Asn Phe His Tyr Gly Ser Val Val Thr Tyr Arg Cys Asn Pro Gly Ser
        595                 600                 605

Gly Gly Arg Lys Val Phe Glu Leu Val Gly Glu Pro Ser Ile Tyr Cys
        610                 615                 620

Thr Ser Asn Asp Asp Gln Val Gly Ile Trp Ser Gly Pro Ala Pro Gln
625                 630                 635                 640

Cys Ile Ile Pro Asn Lys Cys Thr Pro Pro Asn Val Glu Asn Gly Ile
                645                 650                 655

Leu Val Ser Asp Asn Arg Ser Leu Phe Ser Leu Asn Glu Val Val Glu
            660                 665                 670

Phe Arg Cys Gln Pro Gly Phe Val Met Lys Gly Pro Arg Arg Val Lys
        675                 680                 685

Cys Gln Ala Leu Asn Lys Trp Glu Pro Glu Leu Pro Ser Cys Ser Arg
    690                 695                 700

Val Cys Gln Pro Pro Pro Asp Val Leu His Ala Glu Arg Thr Gln Arg
705                 710                 715                 720

Asp Lys Asp Asn Phe Ser Pro Gly Gln Glu Val Phe Tyr Ser Cys Glu
                725                 730                 735

Pro Gly Tyr Asp Leu Arg Gly Ala Ala Ser Met Arg Cys Thr Pro Gln
            740                 745                 750

Gly Asp Trp Ser Pro Ala Ala Pro Thr Cys Glu Val Lys Ser Cys Asp
        755                 760                 765

Asp Phe Met Gly Gln Leu Leu Asn Gly Arg Val Leu Phe Pro Val Asn
    770                 775                 780

Leu Gln Leu Gly Ala Lys Val Asp Phe Val Cys Asp Glu Gly Phe Gln
785                 790                 795                 800

Leu Lys Gly Ser Ser Ala Ser Tyr Cys Val Leu Ala Gly Met Glu Ser
                805                 810                 815

Leu Trp Asn Ser Ser Val Pro Val Cys Glu Gln Ile Phe Cys Pro Ser
            820                 825                 830

Pro Pro Val Ile Pro Asn Gly Arg His Thr Gly Lys Pro Leu Glu Val
        835                 840                 845

Phe Pro Phe Gly Lys Ala Val Asn Tyr Thr Cys Asp Pro His Pro Asp
    850                 855                 860

Arg Gly Thr Ser Phe Asp Leu Ile Gly Glu Ser Thr Ile Arg Cys Thr
865                 870                 875                 880

Ser Asp Pro Gln Gly Asn Gly Val Trp Ser Ser Pro Ala Pro Arg Cys
                885                 890                 895

Gly Ile Leu Gly His Cys Gln Ala Pro Asp His Phe Leu Phe Ala Lys
            900                 905                 910

Leu Lys Thr Gln Thr Asn Ala Ser Asp Phe Pro Ile Gly Thr Ser Leu
        915                 920                 925

Lys Tyr Glu Cys Arg Pro Glu Tyr Tyr Gly Arg Pro Phe Ser Ile Thr
    930                 935                 940

Cys Leu Asp Asn Leu Val Trp Ser Ser Pro Lys Asp Val Cys Lys Arg
945                 950                 955                 960

Lys Ser Cys Lys Thr Pro Pro Asp Pro Val Asn Gly Met Val His Val
                965                 970                 975

Ile Thr Asp Ile Gln Val Gly Ser Arg Ile Asn Tyr Ser Cys Thr Thr
            980                 985                 990
```

-continued

```
Gly His Arg Leu Ile Gly His Ser  Ser Ala Glu Cys Ile  Leu Ser Gly
        995                1000                  1005

Asn Thr  Ala His Trp Ser Thr  Lys Pro Pro Ile Cys  Gln Arg Ile
   1010               1015                  1020

Pro Cys  Gly Leu Pro Pro Thr  Ile Ala Asn Gly Asp  Phe Ile Ser
   1025               1030                  1035

Thr Asn  Arg Glu Asn Phe His  Tyr Gly Ser Val Val  Thr Tyr Arg
   1040               1045                  1050

Cys Asn  Leu Gly Ser Arg Gly  Arg Lys Val Phe Glu  Leu Val Gly
   1055               1060                  1065

Glu Pro  Ser Ile Tyr Cys Thr  Ser Asn Asp Asp Gln  Val Gly Ile
   1070               1075                  1080

Trp Ser  Gly Pro Ala Pro Gln  Cys Ile Ile Pro Asn  Lys Cys Thr
   1085               1090                  1095

Pro Pro  Asn Val Glu Asn Gly  Ile Leu Val Ser Asp  Asn Arg Ser
   1100               1105                  1110

Leu Phe  Ser Leu Asn Glu Val  Val Glu Phe Arg Cys  Gln Pro Gly
   1115               1120                  1125

Phe Val  Met Lys Gly Pro Arg  Arg Val Lys Cys Gln  Ala Leu Asn
   1130               1135                  1140

Lys Trp  Glu Pro Glu Leu Pro  Ser Cys Ser Arg Val  Cys Gln Pro
   1145               1150                  1155

Pro Pro  Glu Ile Leu His Gly  Glu His Thr Pro Ser  His Gln Asp
   1160               1165                  1170

Asn Phe  Ser Pro Gly Gln Glu  Val Phe Tyr Ser Cys  Glu Pro Gly
   1175               1180                  1185

Tyr Asp  Leu Arg Gly Ala Ala  Ser Leu His Cys Thr  Pro Gln Gly
   1190               1195                  1200

Asp Trp  Ser Pro Glu Ala Pro  Arg Cys Ala Val Lys  Ser Cys Asp
   1205               1210                  1215

Asp Phe  Leu Gly Gln Leu Pro  His Gly Arg Val Leu  Phe Pro Leu
   1220               1225                  1230

Asn Leu  Gln Leu Gly Ala Lys  Val Ser Phe Val Cys  Asp Glu Gly
   1235               1240                  1245

Phe Arg  Leu Lys Gly Ser Ser  Val Ser His Cys Val  Leu Val Gly
   1250               1255                  1260

Met Arg  Ser Leu Trp Asn Asn  Ser Val Pro Val Cys  Glu His Ile
   1265               1270                  1275

Phe Cys  Pro Asn Pro Pro Ala  Ile Leu Asn Gly Arg  His Thr Gly
   1280               1285                  1290

Thr Pro  Ser Gly Asp Ile Pro  Tyr Gly Lys Glu Ile  Ser Tyr Thr
   1295               1300                  1305

Cys Asp  Pro His Pro Asp Arg  Gly Met Thr Phe Asn  Leu Ile Gly
   1310               1315                  1320

Glu Ser  Thr Ile Arg Cys Thr  Ser Asp Pro His Gly  Asn Gly Val
   1325               1330                  1335

Trp Ser  Ser Pro Ala Pro Arg  Cys Glu Leu Ser Val  Arg Ala Gly
   1340               1345                  1350

His Cys  Lys Thr Pro Glu Gln  Phe Pro Phe Ala Ser  Pro Thr Ile
   1355               1360                  1365

Pro Ile  Asn Asp Phe Glu Phe  Pro Val Gly Thr Ser  Leu Asn Tyr
   1370               1375                  1380

Glu Cys  Arg Pro Gly Tyr Phe  Gly Lys Met Phe Ser  Ile Ser Cys
   1385               1390                  1395
```

```
Leu Glu Asn Leu Val Trp Ser Ser Val Glu Asp Asn Cys Arg Arg
    1400            1405            1410

Lys Ser Cys Gly Pro Pro Glu Pro Phe Asn Gly Met Val His
    1415            1420            1425

Ile Asn Thr Asp Thr Gln Phe Gly Ser Thr Val Asn Tyr Ser Cys
    1430            1435            1440

Asn Glu Gly Phe Arg Leu Ile Gly Ser Pro Ser Thr Thr Cys Leu
    1445            1450            1455

Val Ser Gly Asn Asn Val Thr Trp Asp Lys Lys Ala Pro Ile Cys
    1460            1465            1470

Glu Ile Ile Ser Cys Glu Pro Pro Thr Ile Ser Asn Gly Asp
    1475            1480            1485

Phe Tyr Ser Asn Asn Arg Thr Ser Phe His Asn Gly Thr Val Val
    1490            1495            1500

Thr Tyr Gln Cys His Thr Gly Pro Asp Gly Glu Gln Leu Phe Glu
    1505            1510            1515

Leu Val Gly Glu Arg Ser Ile Tyr Cys Thr Ser Lys Asp Asp Gln
    1520            1525            1530

Val Gly Val Trp Ser Ser Pro Pro Arg Cys Ile Ser Thr Asn
    1535            1540            1545

Lys Cys Thr Ala Pro Glu Val Glu Asn Ala Ile Arg Val Pro Gly
    1550            1555            1560

Asn Arg Ser Phe Phe Ser Leu Thr Glu Ile Ile Arg Phe Arg Cys
    1565            1570            1575

Gln Pro Gly Phe Val Met Val Gly Ser His Thr Val Gln Cys Gln
    1580            1585            1590

Thr Asn Gly Arg Trp Gly Pro Lys Leu Pro His Cys Ser Arg Val
    1595            1600            1605

Cys Gln Pro Pro Pro Glu Ile Leu His Gly Glu His Thr Leu Ser
    1610            1615            1620

His Gln Asp Asn Phe Ser Pro Gly Gln Glu Val Phe Tyr Ser Cys
    1625            1630            1635

Glu Pro Ser Tyr Asp Leu Arg Gly Ala Ala Ser Leu His Cys Thr
    1640            1645            1650

Pro Gln Gly Asp Trp Ser Pro Glu Ala Pro Arg Cys Thr Val Lys
    1655            1660            1665

Ser Cys Asp Asp Phe Leu Gly Gln Leu Pro His Gly Arg Val Leu
    1670            1675            1680

Leu Pro Leu Asn Leu Gln Leu Gly Ala Lys Val Ser Phe Val Cys
    1685            1690            1695

Asp Glu Gly Phe Arg Leu Lys Gly Arg Ser Ala Ser His Cys Val
    1700            1705            1710

Leu Ala Gly Met Lys Ala Leu Trp Asn Ser Ser Val Pro Val Cys
    1715            1720            1725

Glu Gln Ile Phe Cys Pro Asn Pro Pro Ala Ile Leu Asn Gly Arg
    1730            1735            1740

His Thr Gly Thr Pro Phe Gly Asp Ile Pro Tyr Gly Lys Glu Ile
    1745            1750            1755

Ser Tyr Ala Cys Asp Thr His Pro Asp Arg Gly Met Thr Phe Asn
    1760            1765            1770

Leu Ile Gly Glu Ser Ser Ile Arg Cys Thr Ser Asp Pro Gln Gly
    1775            1780            1785

Asn Gly Val Trp Ser Ser Pro Ala Pro Arg Cys Glu Leu Ser Val
```

-continued

```
                1790                1795                1800

Pro Ala Ala Cys Pro His Pro Lys Ile Gln Asn Gly His Tyr
    1805                1810                1815

Ile Gly Gly His Val Ser Leu Tyr Leu Pro Gly Met Thr Ile Ser
    1820                1825                1830

Tyr Thr Cys Asp Pro Gly Tyr Leu Leu Val Gly Lys Gly Phe Ile
    1835                1840                1845

Phe Cys Thr Asp Gln Gly Ile Trp Ser Gln Leu Asp His Tyr Cys
    1850                1855                1860

Lys Glu Val Asn Cys Ser Phe Pro Leu Phe Met Asn Gly Ile Ser
    1865                1870                1875

Lys Glu Leu Glu Met Lys Lys Val Tyr His Tyr Gly Asp Tyr Val
    1880                1885                1890

Thr Leu Lys Cys Glu Asp Gly Tyr Thr Leu Glu Gly Ser Pro Trp
    1895                1900                1905

Ser Gln Cys Gln Ala Asp Asp Arg Trp Asp Pro Pro Leu Ala Lys
    1910                1915                1920

Cys Thr Ser Arg Ala His Asp Ala Leu Ile Val Gly Thr Leu Ser
    1925                1930                1935

Gly Thr Ile Phe Phe Ile Leu Leu Ile Ile Phe Leu Ser Trp Ile
    1940                1945                1950

Ile Leu Lys His Arg Lys Gly Asn Asn Ala His Glu Asn Pro Lys
    1955                1960                1965

Glu Val Ala Ile His Leu His Ser Gln Gly Gly Ser Ser Val His
    1970                1975                1980

Pro Arg Thr Leu Gln Thr Asn Glu Glu Asn Ser Arg Val Leu Pro
    1985                1990                1995

<210> SEQ ID NO 3
<211> LENGTH: 1931
<212> TYPE: PRT
<213> ORGANISM: Homo sapiens
<220> FEATURE:
<221> NAME/KEY: MISC_FEATURE
<222> LOCATION: (1)..(1931)
<223> OTHER INFORMATION: soluble CR1 polypeptide

<400> SEQUENCE: 3

Gln Cys Asn Ala Pro Glu Trp Leu Pro Phe Ala Arg Pro Thr Asn Leu
1               5                   10                  15

Thr Asp Glu Phe Glu Phe Pro Ile Gly Thr Tyr Leu Asn Tyr Glu Cys
                20                  25                  30

Arg Pro Gly Tyr Ser Gly Arg Pro Phe Ser Ile Ile Cys Leu Lys Asn
            35                  40                  45

Ser Val Trp Thr Gly Ala Lys Asp Arg Cys Arg Arg Lys Ser Cys Arg
    50                  55                  60

Asn Pro Pro Asp Pro Val Asn Gly Met Val His Val Ile Lys Gly Ile
65                  70                  75                  80

Gln Phe Gly Ser Gln Ile Lys Tyr Ser Cys Thr Lys Gly Tyr Arg Leu
                85                  90                  95

Ile Gly Ser Ser Ser Ala Thr Cys Ile Ile Ser Gly Asp Thr Val Ile
            100                 105                 110

Trp Asp Asn Glu Thr Pro Ile Cys Asp Arg Ile Pro Cys Gly Leu Pro
        115                 120                 125

Pro Thr Ile Thr Asn Gly Asp Phe Ile Ser Thr Asn Arg Glu Asn Phe
    130                 135                 140
```

-continued

```
His Tyr Gly Ser Val Val Thr Tyr Arg Cys Asn Pro Gly Ser Gly Gly
145                 150                 155                 160

Arg Lys Val Phe Glu Leu Val Gly Glu Pro Ser Ile Tyr Cys Thr Ser
                165                 170                 175

Asn Asp Asp Gln Val Gly Ile Trp Ser Gly Pro Ala Pro Gln Cys Ile
            180                 185                 190

Ile Pro Asn Lys Cys Thr Pro Pro Asn Val Glu Asn Gly Ile Leu Val
        195                 200                 205

Ser Asp Asn Arg Ser Leu Phe Ser Leu Asn Glu Val Glu Phe Arg
210                 215                 220

Cys Gln Pro Gly Phe Val Met Lys Gly Pro Arg Val Lys Cys Gln
225                 230                 235                 240

Ala Leu Asn Lys Trp Glu Pro Glu Leu Pro Ser Cys Ser Arg Val Cys
                245                 250                 255

Gln Pro Pro Pro Asp Val Leu His Ala Glu Arg Thr Gln Arg Asp Lys
                260                 265                 270

Asp Asn Phe Ser Pro Gly Gln Glu Val Phe Tyr Ser Cys Glu Pro Gly
            275                 280                 285

Tyr Asp Leu Arg Gly Ala Ala Ser Met Arg Cys Thr Pro Gln Gly Asp
290                 295                 300

Trp Ser Pro Ala Ala Pro Thr Cys Glu Val Lys Ser Cys Asp Asp Phe
305                 310                 315                 320

Met Gly Gln Leu Leu Asn Gly Arg Val Leu Phe Pro Val Asn Leu Gln
                325                 330                 335

Leu Gly Ala Lys Val Asp Phe Val Cys Asp Glu Gly Phe Gln Leu Lys
                340                 345                 350

Gly Ser Ser Ala Ser Tyr Cys Val Leu Ala Gly Met Glu Ser Leu Trp
            355                 360                 365

Asn Ser Ser Val Pro Val Cys Glu Gln Ile Phe Cys Pro Ser Pro Pro
        370                 375                 380

Val Ile Pro Asn Gly Arg His Thr Gly Lys Pro Leu Glu Val Phe Pro
385                 390                 395                 400

Phe Gly Lys Ala Val Asn Tyr Thr Cys Asp Pro His Pro Asp Arg Gly
                405                 410                 415

Thr Ser Phe Asp Leu Ile Gly Glu Ser Thr Ile Arg Cys Thr Ser Asp
                420                 425                 430

Pro Gln Gly Asn Gly Val Trp Ser Ser Pro Ala Pro Arg Cys Gly Ile
            435                 440                 445

Leu Gly His Cys Gln Ala Pro Asp His Phe Leu Phe Ala Lys Leu Lys
        450                 455                 460

Thr Gln Thr Asn Ala Ser Asp Phe Pro Ile Gly Thr Ser Leu Lys Tyr
465                 470                 475                 480

Glu Cys Arg Pro Glu Tyr Tyr Gly Arg Pro Phe Ser Ile Thr Cys Leu
                485                 490                 495

Asp Asn Leu Val Trp Ser Ser Pro Lys Asp Val Cys Lys Arg Lys Ser
            500                 505                 510

Cys Lys Thr Pro Pro Asp Pro Val Asn Gly Met Val His Val Ile Thr
        515                 520                 525

Asp Ile Gln Val Gly Ser Arg Ile Asn Tyr Ser Cys Thr Thr Gly His
530                 535                 540

Arg Leu Ile Gly His Ser Ser Ala Glu Cys Ile Leu Ser Gly Asn Ala
545                 550                 555                 560

Ala His Trp Ser Thr Lys Pro Pro Ile Cys Gln Arg Ile Pro Cys Gly
                565                 570                 575
```

```
Leu Pro Pro Thr Ile Ala Asn Gly Asp Phe Ile Ser Thr Asn Arg Glu
            580                 585                 590

Asn Phe His Tyr Gly Ser Val Val Thr Tyr Arg Cys Asn Pro Gly Ser
        595                 600                 605

Gly Gly Arg Lys Val Phe Glu Leu Val Gly Glu Pro Ser Ile Tyr Cys
    610                 615                 620

Thr Ser Asn Asp Asp Gln Val Gly Ile Trp Ser Gly Pro Ala Pro Gln
625                 630                 635                 640

Cys Ile Ile Pro Asn Lys Cys Thr Pro Pro Asn Val Glu Asn Gly Ile
                645                 650                 655

Leu Val Ser Asp Asn Arg Ser Leu Phe Ser Leu Asn Glu Val Val Glu
                660                 665                 670

Phe Arg Cys Gln Pro Gly Phe Val Met Lys Gly Pro Arg Arg Val Lys
                675                 680                 685

Cys Gln Ala Leu Asn Lys Trp Glu Pro Glu Leu Pro Ser Cys Ser Arg
690                 695                 700

Val Cys Gln Pro Pro Asp Val Leu His Ala Glu Arg Thr Gln Arg
705                 710                 715                 720

Asp Lys Asp Asn Phe Ser Pro Gly Gln Glu Val Phe Tyr Ser Cys Glu
                    725                 730                 735

Pro Gly Tyr Asp Leu Arg Gly Ala Ala Ser Met Arg Cys Thr Pro Gln
                740                 745                 750

Gly Asp Trp Ser Pro Ala Ala Pro Thr Cys Glu Val Lys Ser Cys Asp
            755                 760                 765

Asp Phe Met Gly Gln Leu Leu Asn Gly Arg Val Leu Phe Pro Val Asn
770                 775                 780

Leu Gln Leu Gly Ala Lys Val Asp Phe Val Cys Asp Glu Gly Phe Gln
785                 790                 795                 800

Leu Lys Gly Ser Ser Ala Ser Tyr Cys Val Leu Ala Gly Met Glu Ser
                805                 810                 815

Leu Trp Asn Ser Ser Val Pro Val Cys Glu Gln Ile Phe Cys Pro Ser
                820                 825                 830

Pro Pro Val Ile Pro Asn Gly Arg His Thr Gly Lys Pro Leu Glu Val
                835                 840                 845

Phe Pro Phe Gly Lys Ala Val Asn Tyr Thr Cys Asp Pro His Pro Asp
            850                 855                 860

Arg Gly Thr Ser Phe Asp Leu Ile Gly Glu Ser Thr Ile Arg Cys Thr
865                 870                 875                 880

Ser Asp Pro Gln Gly Asn Gly Val Trp Ser Ser Pro Ala Pro Arg Cys
                885                 890                 895

Gly Ile Leu Gly His Cys Gln Ala Pro Asp His Phe Leu Phe Ala Lys
                900                 905                 910

Leu Lys Thr Gln Thr Asn Ala Ser Asp Phe Pro Ile Gly Thr Ser Leu
            915                 920                 925

Lys Tyr Glu Cys Arg Pro Glu Tyr Tyr Gly Arg Pro Phe Ser Ile Thr
            930                 935                 940

Cys Leu Asp Asn Leu Val Trp Ser Ser Pro Lys Asp Val Cys Lys Arg
945                 950                 955                 960

Lys Ser Cys Lys Thr Pro Pro Asp Pro Val Asn Gly Met Val His Val
                965                 970                 975

Ile Thr Asp Ile Gln Val Gly Ser Arg Ile Asn Tyr Ser Cys Thr Thr
                980                 985                 990

Gly His Arg Leu Ile Gly His Ser  Ser Ala Glu Cys Ile  Leu Ser Gly
```

-continued

```
                995                 1000                1005
Asn Thr Ala His Trp Ser Thr Lys Pro Pro Ile Cys Gln Arg Ile
1010                1015                1020

Pro Cys Gly Leu Pro Pro Thr Ile Ala Asn Gly Asp Phe Ile Ser
1025                1030                1035

Thr Asn Arg Glu Asn Phe His Tyr Gly Ser Val Val Thr Tyr Arg
1040                1045                1050

Cys Asn Leu Gly Ser Arg Gly Arg Lys Val Phe Glu Leu Val Gly
1055                1060                1065

Glu Pro Ser Ile Tyr Cys Thr Ser Asn Asp Asp Gln Val Gly Ile
1070                1075                1080

Trp Ser Gly Pro Ala Pro Gln Cys Ile Ile Pro Asn Lys Cys Thr
1085                1090                1095

Pro Pro Asn Val Glu Asn Gly Ile Leu Val Ser Asp Asn Arg Ser
1100                1105                1110

Leu Phe Ser Leu Asn Glu Val Val Glu Phe Arg Cys Gln Pro Gly
1115                1120                1125

Phe Val Met Lys Gly Pro Arg Arg Val Lys Cys Gln Ala Leu Asn
1130                1135                1140

Lys Trp Glu Pro Glu Leu Pro Ser Cys Ser Arg Val Cys Gln Pro
1145                1150                1155

Pro Pro Glu Ile Leu His Gly Glu His Thr Pro Ser His Gln Asp
1160                1165                1170

Asn Phe Ser Pro Gly Gln Glu Val Phe Tyr Ser Cys Glu Pro Gly
1175                1180                1185

Tyr Asp Leu Arg Gly Ala Ala Ser Leu His Cys Thr Pro Gln Gly
1190                1195                1200

Asp Trp Ser Pro Glu Ala Pro Arg Cys Ala Val Lys Ser Cys Asp
1205                1210                1215

Asp Phe Leu Gly Gln Leu Pro His Gly Arg Val Leu Phe Pro Leu
1220                1225                1230

Asn Leu Gln Leu Gly Ala Lys Val Ser Phe Val Cys Asp Glu Gly
1235                1240                1245

Phe Arg Leu Lys Gly Ser Ser Val Ser His Cys Val Leu Val Gly
1250                1255                1260

Met Arg Ser Leu Trp Asn Asn Ser Val Pro Val Cys Glu His Ile
1265                1270                1275

Phe Cys Pro Asn Pro Pro Ala Ile Leu Asn Gly Arg His Thr Gly
1280                1285                1290

Thr Pro Ser Gly Asp Ile Pro Tyr Gly Lys Glu Ile Ser Tyr Thr
1295                1300                1305

Cys Asp Pro His Pro Asp Arg Gly Met Thr Phe Asn Leu Ile Gly
1310                1315                1320

Glu Ser Thr Ile Arg Cys Thr Ser Asp Pro His Gly Asn Gly Val
1325                1330                1335

Trp Ser Ser Pro Ala Pro Arg Cys Glu Leu Ser Val Arg Ala Gly
1340                1345                1350

His Cys Lys Thr Pro Glu Gln Phe Pro Phe Ala Ser Pro Thr Ile
1355                1360                1365

Pro Ile Asn Asp Phe Glu Phe Pro Val Gly Thr Ser Leu Asn Tyr
1370                1375                1380

Glu Cys Arg Pro Gly Tyr Phe Gly Lys Met Phe Ser Ile Ser Cys
1385                1390                1395
```

```
Leu Glu Asn Leu Val Trp Ser Ser Val Glu Asp Asn Cys Arg Arg
    1400            1405            1410

Lys Ser Cys Gly Pro Pro Glu Pro Phe Asn Gly Met Val His
    1415            1420            1425

Ile Asn Thr Asp Thr Gln Phe Gly Ser Thr Val Asn Tyr Ser Cys
    1430            1435            1440

Asn Glu Gly Phe Arg Leu Ile Gly Ser Pro Ser Thr Thr Cys Leu
    1445            1450            1455

Val Ser Gly Asn Asn Val Thr Trp Asp Lys Lys Ala Pro Ile Cys
    1460            1465            1470

Glu Ile Ile Ser Cys Glu Pro Pro Thr Ile Ser Asn Gly Asp
    1475            1480            1485

Phe Tyr Ser Asn Asn Arg Thr Ser Phe His Asn Gly Thr Val Val
    1490            1495            1500

Thr Tyr Gln Cys His Thr Gly Pro Asp Gly Glu Gln Leu Phe Glu
    1505            1510            1515

Leu Val Gly Glu Arg Ser Ile Tyr Cys Thr Ser Lys Asp Asp Gln
    1520            1525            1530

Val Gly Val Trp Ser Ser Pro Pro Pro Arg Cys Ile Ser Thr Asn
    1535            1540            1545

Lys Cys Thr Ala Pro Glu Val Glu Asn Ala Ile Arg Val Pro Gly
    1550            1555            1560

Asn Arg Ser Phe Phe Ser Leu Thr Glu Ile Ile Arg Phe Arg Cys
    1565            1570            1575

Gln Pro Gly Phe Val Met Val Gly Ser His Thr Val Gln Cys Gln
    1580            1585            1590

Thr Asn Gly Arg Trp Gly Pro Lys Leu Pro His Cys Ser Arg Val
    1595            1600            1605

Cys Gln Pro Pro Pro Glu Ile Leu His Gly Glu His Thr Leu Ser
    1610            1615            1620

His Gln Asp Asn Phe Ser Pro Gly Gln Glu Val Phe Tyr Ser Cys
    1625            1630            1635

Glu Pro Ser Tyr Asp Leu Arg Gly Ala Ala Ser Leu His Cys Thr
    1640            1645            1650

Pro Gln Gly Asp Trp Ser Pro Glu Ala Pro Arg Cys Thr Val Lys
    1655            1660            1665

Ser Cys Asp Asp Phe Leu Gly Gln Leu Pro His Gly Arg Val Leu
    1670            1675            1680

Leu Pro Leu Asn Leu Gln Leu Gly Ala Lys Val Ser Phe Val Cys
    1685            1690            1695

Asp Glu Gly Phe Arg Leu Lys Gly Arg Ser Ala Ser His Cys Val
    1700            1705            1710

Leu Ala Gly Met Lys Ala Leu Trp Asn Ser Ser Val Pro Val Cys
    1715            1720            1725

Glu Gln Ile Phe Cys Pro Asn Pro Pro Ala Ile Leu Asn Gly Arg
    1730            1735            1740

His Thr Gly Thr Pro Phe Gly Asp Ile Pro Tyr Gly Lys Glu Ile
    1745            1750            1755

Ser Tyr Ala Cys Asp Thr His Pro Asp Arg Gly Met Thr Phe Asn
    1760            1765            1770

Leu Ile Gly Glu Ser Ser Ile Arg Cys Thr Ser Asp Pro Gln Gly
    1775            1780            1785

Asn Gly Val Trp Ser Ser Pro Ala Pro Arg Cys Glu Leu Ser Val
    1790            1795            1800
```

-continued

```
Pro Ala Ala Cys Pro His Pro Pro Lys Ile Gln Asn Gly His Tyr
1805                1810                1815

Ile Gly Gly His Val Ser Leu Tyr Leu Pro Gly Met Thr Ile Ser
1820                1825                1830

Tyr Ile Cys Asp Pro Gly Tyr Leu Leu Val Gly Lys Gly Phe Ile
1835                1840                1845

Phe Cys Thr Asp Gln Gly Ile Trp Ser Gln Leu Asp His Tyr Cys
1850                1855                1860

Lys Glu Val Asn Cys Ser Phe Pro Leu Phe Met Asn Gly Ile Ser
1865                1870                1875

Lys Glu Leu Glu Met Lys Lys Val Tyr His Tyr Gly Asp Tyr Val
1880                1885                1890

Thr Leu Lys Cys Glu Asp Gly Tyr Thr Leu Glu Gly Ser Pro Trp
1895                1900                1905

Ser Gln Cys Gln Ala Asp Asp Arg Trp Asp Pro Pro Leu Ala Lys
1910                1915                1920

Cys Thr Ser Arg Ala His Asp Ala
1925                1930
```

TREATMENT FOR AGE-RELATED MACULAR DEGENERATION AND OTHER DISEASES OF THE EYE

This application is a United States national stage filing under 35 U.S.C. §371 of international (PCT) application No. PCT/US2007/022276, filed Oct. 19, 2007 and designating the US, which international application claims priority to U.S. provisional application Nos. 60/928,046, filed May 7, 2007, and 60/853,201, filed Oct. 20, 2006.

FIELD OF THE INVENTION

The present invention relates to pharmaceutical compositions for treatment of diseases of the eye characterized by undesired or abnormal choroidal neovascularization, particularly age-related macular degeneration (AMD). In particular, the invention relates to the use of pharmaceutical compositions comprising complement inhibitor proteins, in particular a soluble complement receptor type I (sCR1), which have been found to be useful in the treatment of AMD in a relevant animal model.

BACKGROUND OF THE INVENTION

Age-related macular degeneration (AMD) is a major cause of central visual loss and is the leading cause of blindness in people over the age of 60 in the United States. The National Eye Institute estimates that there are approximately 1.6 million people in the United States with late AMD. (See, e.g., "Vision Problems in the U.S.," US Dept. of Health and Human Services, Nat'l Institutes of Health, Nat'l Eye Institute, 2002, www.nei.nih.gov.)

AMD is a complex disease whose risk factors include aging, family history of AMD, smoking, hypertension, obesity, diet, and ethnicity, and there is a strong indication of a genetic contribution. Ambati et al., *Surv. Ophthalmol.*, 48:257 (2003). Two major clinical phenotypes of AMD are recognized: a nonexudative (thy) type and an exudative (wet) type.

The dry form of AMD is associated with cell death of the light-sensitive macular part of the retina, which is required for fine vision used in activities such as reading, driving or recognizing faces. Over time, as less of the macula functions, central vision in the affected eye can be lost gradually. One of the most common early signs of dry AMD is the appearance of drusen. Drusen are yellow deposits under the retina and are often found in people over the age of 60. Dry AMD has three stages, all of which may occur in one or both eyes: early AMD, intermediate AMD, and advanced AMD. Early and intermediate AMD are characterized by the presence of small or medium-sized drusen, and persons suffering from early and intermediate AMD may require additional light when reading and experience a blurred spot in the center of their vision. Persons suffering from advanced AMD, in addition to the presence of medium or large-sized drusen, exhibit a breakdown of light-sensitive cells and supporting tissue in the central retinal area.

The wet form of AMD is caused by growth of abnormal blood vessels, also known as choroidal neovascularization (CNV), under the macula. These vessels leak blood and fluid which raises the macula from its normal position at the back of the eye and causes scar tissue formation, which destroys the central retina and results in deterioration of sight. The pathogenesis of new choroidal blood vessel formation which characterizes wet AMD is not completely understood. Inflammation, ischemia, and local production of angiogenic factors are all thought to be important in pathogenesis. With wet AMD, loss of central vision can occur quickly. Wet AMD is considered to be advanced AMD and is more severe than the dry form.

The dry form of AMD is more prevalent; about 85% of all people with intermediate and advanced AMD have the dry form. However, about two-thirds of all patients with advanced AMD have the wet form. It is believed that all patients who have the wet form of AMD had the dry form first. (See, "Age-Related Macular Degeneration: What You Should Know," US Dept. of Health and Human Services, Nat'l Institutes of Health, Nat'l Eye Institute, Publn. No. 03-2294, 2003.)

Although the direct cause of AMD remains unknown, recent studies have pointed to a number of single nucleotide polymorphisms (SNPs) in and around the gene for complement Factor H which appear to predispose people to AMD. Patients exhibiting this mutation have been linked to an increased likelihood of developing the disease. See, Hageman et al., 2005, *PNAS*, 102(20): 7227-7232; Klein et al., 2005, *Science*, 308: 385-388; Haines et al., 2005, *Science*, 308: 419-421. See, also, Edwards, 2005, *Science*, 308: 421; Li, 2006, *Nature Genetics*, 38: 1049; Despriet, 2006, *JAMA*, 296: 301; Mailer, 2006, *Nature Genetics*, 38: 1005.

Factor H is one of the complement regulatory proteins which down-regulates complement activation and is a member of the family of genes known as the Regulators of Complement Activation (RCA) gene locus encoded on human chromosome 1q32. The complement system is a group of proteins that constitutes about 10 percent of the globulins in normal serum of humans (Hood et al., *Immunology*, 2d Ed. (The Benjamin/Cummings Publishing Co., Menlo Park, Calif., 1984), p. 339), and it plays an important role in the mediation of immune and allergic reactions. The complement system is a major component of innate immunity and is a central host defense against infection. The activation of complement components leads to the generation of a group of factors, including chemotactic peptides that mediate the inflammation associated with complement-dependent diseases.

Activation of the complement cascade may occur via the classical pathway, involving antigen-antibody complexes; by the lectin pathway, or by the alternative pathway, involving the recognition of certain cell wall polysaccharides. The activities mediated by activated complement proteins include lysis of microorganisms, chemotaxis, opsonization, stimulation of vascular and other smooth muscle cells, degranulation of mast cells, increased permeability of small blood vessels, directed migration of leukocytes, and activation of B lymphocytes and macrophages. The membrane attack complex (MAC) is the final product of the activated complement cascade. It is a lytic multi-protein complex that is lethal to pathogens and, at sublytic levels, causes the release of cytokines and growth factors such as beta-FGF and VEGF from nucleated cells (e.g., smooth muscle cells, endothelial cells).

Factor H is one of a dozen or so proteins of the complement system having a repeating structural motif known as a short consensus repeat (SCR) and sharing a capacity for interacting with activation products of the complement components C3 and C4, as well as other components of the complement system. Ahearn et al., 1989, *Adv. Immunol.*, 46:183-219. During complement activation, biologically active peptide fragments, the anaphylatoxins C3a, C4a, and C5a, are released from complement components C3, C4, and C5. Hugh, 1981, *CRC Crit. Rev. Immunol.*, 1:321. Factor H and other complement regulatory proteins such as C4-binding protein (C4-BP), decay accelerating factor (DAF), membrane cofactor protein (MCP), and complement receptor type I (CR1) have a negative regulatory activity and are able to block one or both of the complement activation pathways.

Current treatments for AMD are limited. No treatment for advanced dry AMD exists. However, the transition from intermediate AMD to advanced AMD can be delayed and possibly prevented by taking a specific high-dose formulation of antioxidants and zinc. Research has shown that a daily intake of supplements, including: vitamin C (500 milligrams); vitamin E 400 IU; beta-carotene (15 milligrams); zinc (as zinc oxide) (80 milligrams); and copper (as cupric oxide) (2 milligrams), reduced the risk of patients advancing from intermediate AMD to advanced AMD by 25%, and reduced the risk of vision loss by 19%. (www.amd.org).

Currently there are only four treatments approved by the FDA for wet AMD: laser surgery, photodynamic therapy (PDT), and the drugs Macugen® pegaptanib sodium and Lucentis™ ranibizumab intravitreal injections. Laser, PDT and pegaptanib may slow the rate of vision decline and/or stop vision loss. Pegaptanib (Macugen®, Eyetech Pharmaceuticals Inc. and Pfizer Inc.), is approved for treatment of wet AMD is a pegylated oligonucleotide aptamer targeting VEGF. Ranibizumab (Lucentis™, Genentech/Novartis), an antibody fragment targeting VEGF, has recently been approved by FDA for the treatment of wet AMD.

Laser surgery attempts to destroy the fragile, leaky blood vessels using a high energy beam of light. This treatment, however, may also destroy some surrounding healthy tissue and therefore actually contribute to further vision loss. Because of this, only a small percentage of people with wet AMD can be treated with laser surgery.

Photodynamic therapy also attempts to destroy the newly formed blood vessels in the patient's eye. Verteporfin (marketed in the US by Novartis under the name Visudyne®) is injected into the patient's arm. The drug travels through the patient's body, "sticking" to the surface of new blood vessels. A light is then shone in the patient's eye, which activates the drug, which in turn destroys the new blood vessel. Photodynamic therapy merely temporarily slows the rate of vision loss; it does not stop vision loss or restore vision. Moreover, because the drug is activated by light, the patient must avoid sunlight and bright indoor lights for five days after treatment.

Genetic research continues to illuminate more treatment options. For example, in a study released in September 1997, scientists reported that 16% of 167 patients with dry AMD had a defect in a gene called ABCR. See, Allikmets et al., 1997, *Science,* 277(5333): 1805-7. However, the fact that 84% of the patients suffering from dry AMD in the study did not have the ABCR gene defect indicates that further research is needed. Other family-based whole-genome linkage scans have identified chromosomal regions that show evidence of linkage to AMD; however, the linkage areas have not been resolved to any causative mutations. See, Klein et al., 2005, *Science,* 308: 385-388.

While the recent studies linking a mutation in a complement regulatory protein (Factor H) to development of AMD (see, Hageman et al., 2005, supra; Klein et al., 2005, supra; Haines et al., 2005, supra; Edwards et al., 2005, supra) raises the question of whether the function of Factor H in regulating complement activation is one factor that might play a role in AMD, there is as yet no evidence that therapeutic administration of complement proteins has any impact on AMD. No treatment or therapy utilizing components of the complement system has been proposed.

Clearly, needs remain for an effective treatment of age-related macular degeneration and like diseases of the eye characterized by undesired or abnormal neovascularization.

SUMMARY OF THE INVENTION

The present invention relates to the use of a complement inhibitory protein for the therapeutic treatment of diseases involving choroidal neovascularization, and in particular, age-related macular degeneration (AMD). More particularly, the invention is directed to the administration of soluble complement receptor type I (sCR1) by intravitreal or systemic administration.

Thus, in one aspect, the present invention provides an intraocular formulation comprising an amount of a complement inhibitory protein, and more particularly a soluble CR1 protein, effective to inhibit complement and a pharmaceutically acceptable vehicle.

Another aspect of the invention relates to a method for treating AMD comprising intraocular administration of an amount of a complement inhibitory protein effective to inhibit complement activity to a mammalian subject suffering from AMD or susceptible to AMD. In this aspect, administration of the complement inhibitory protein can advantageously be intraocular (10), including intravitreal (IVT).

Another aspect of the invention relates to a method for treating AMD comprising systemic administration of an amount of a complement inhibitory protein effective to inhibit complement activity to a mammalian subject suffering from AMD or susceptible to AMD. In this aspect, administration of the complement inhibitory protein may be intravenous (IV), subcutaneous (SC), intramuscular (IM), intra-arterial, intraperitoneal (IP), intrathecal, pulmonary, or oral.

The invention provides for the therapeutic treatment of eye diseases or disorders characterized by choroidal neovascularization, in particular age-related macular degeneration (AMD) but also other eye disorders having shared physiological indicia, such as histoplasmosis, myoptic maculopathy, idiopathic CNV, diabetic retinopathy and Purtscher's retinopathy, etc.

DETAILED DESCRIPTION

Figure 1:
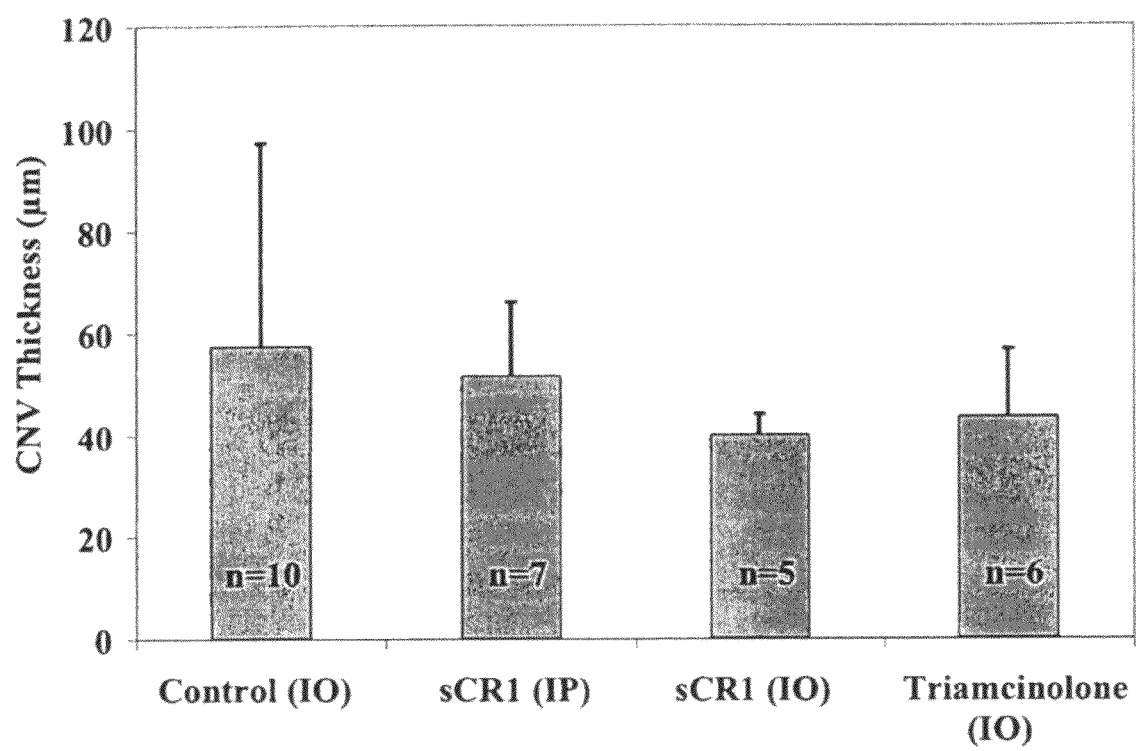
FIG. 1 is a graph showing the choroidal neovascularization thickness (μm) of representative sections of the choroidal burn sites of the test animals.

The present invention is based on the important and surprising discovery that administration of a complement inhibitory protein, in particular soluble CR1, is effective in reducing undesired neovascularization in the eye in a relevant animal model of AMD.

In order that the invention may be more fully understood, the following terms are defined.

The term "complement inhibitory protein" as used herein refers to any of the complement regulatory proteins that have a negative regulatory activity on complement activation. Complement inhibitory proteins useful in the present invention include, specifically, soluble complement receptor type I (sCR1), C4-binding protein (C4-BP), decay accelerating factor (DAF), membrane cofactor protein (MCP), and Factor H. Soluble CR1 polypeptides having at least the C3b and C4b binding sites intact are preferred, as such molecules have the ability to block complement activation via the classical activation pathway and the alternative activation pathway both. Reference to specific complement inhibitory proteins includes fragments of such proteins produced by truncation or splicing-out of unwanted polypeptide segments, so long as complement regulatory activity is retained. Derivatives made by one or more amino acid substitutions or linking to other structures such as carrier proteins or immunoglobulin constant regions are also contemplated, again so long as complement inhibitory activity is retained. In particular, soluble CR1 polypeptides having at least one of the C3b or C4b binding sites intact are preferred, because such molecules will retain the ability to block complement activation via the alternative complement pathway.

As used herein, the terms "soluble complement receptor type I", "soluble CR1 polypeptides" or "soluble CR1" or "sCR1" will be used to refer to portions of full-length human CR1 protein which, in contrast to the native CR1 proteins, are not expressed on the cell surface as transmembrane proteins but nevertheless exhibit a complement regulatory activity such as C3b binding, C4b binding, the ability to inhibit the classical complement activation pathway and/or the alternative complement activation pathway, and/or the lectin complement activation pathway, etc. In particular, CR1 polypeptides which substantially lack a transmembrane region, or, preferably, which comprise all or part of the extracellular domain of CR1 and retain a complement regulatory activity, are soluble CR1 polypeptides. In a preferred embodiment, the soluble CR1 polypeptides useful in the present invention are secreted by a cell in which they are expressed. Suitable soluble CR1 polypeptides and preparations are described in detail, e.g., in U.S. Pat. No. 5,981,481; U.S. Pat. No. 5,456,909; and U.S. Pat. No. 6,193,979, which are incorporated herein by reference. Special mention is made of a soluble CR1 polypeptide having glycosylation modified to exhibit sialyl Lewis X moieties (sCR1-sLe$^x$), as described in U.S. Pat. No. 6,193,979; novel glycoform preparations of soluble CR1 having an increased in vivo half-life described in U.S. Pat. No. 5,456,909; and soluble constructs having two or more CR1 moieties linked to a carrier molecule, e.g., an sCR1-F(ab)2 fusion, as described in U.S. Pat. No. 6,458,360. Also contemplated are soluble CR1 polypeptides having at least one of the C3b or C4b binding sites intact covalently linked to lipopeptides to facilitate localization on cell surfaces, as disclosed in U.S. Pat. No. 6,713,606. More preferably, the method of the invention utilizes a polypeptide comprising the extracellular domain of mature human CR1 (SEQ ID NO:3).

As used herein, the terms "treatment" or "treating" refers to any regimen that alleviates one or more symptoms of a disease or disorder, that inhibits progression of a disease or disorder, that arrests progression or reverses progression (causes regression) of a disease or disorder, or that prevents onset of a disease or disorder. Treatment includes prophylaxis and includes but does not require cure of a disease or disorder.

Macular degeneration is a clinical term that is used to describe a variety of diseases that are all characterized by a progressive loss of central vision associated with abnormalities of Bruch's membrane, the neural retina and the retinal pigment epithelium (RPE). These disorders include very common conditions that affect older patients (age-related macular degeneration or AMD) as well as rarer, earlier-onset dystrophies that in some cases can be detected in the first decade of life (Best, 1905, Z. Augenheilkd., 13:199-212). The term "macular degeneration" as used herein refers to any of a number of conditions in which the retinal macula degenerates or becomes dysfunctional, e.g., as a consequence of decreased growth of cells of the macula, increased death or rearrangement of the cells of the macula (e.g., RPE cells, loss of normal biological function, or a combination of these events). Macular degeneration results in the loss of integrity of the histoarchitecture of the cells of the normal macula and/or the loss of function of the cells of the macula. Any condition which alters or damages the integrity or function of the macula (e.g., damage to the RPE or Bruch's membrane) may be considered to fall within the definition of macular degeneration. Other examples of diseases in which cellular degeneration has been implicated include retinal detachment, chorioretinal degenerations, retinal degenerations, photoreceptor degenerations, RPE degenerations, mucopolysaccharidoses, rod-cone dystrophies, cone-rod dystrophies and cone degenerations.

As used herein, the terms "disease" and "disorder" have the meaning generally known and understood in the art and comprise any abnormal condition in the function or well being of a host individual. A diagnosis of a particular disease or disorder, such macular degeneration and more specifically, age-related macular degeneration, by a healthcare professional may be made by direct examination and/or consideration of results of one or more diagnostic tests. The term "disease of the eye characterized by undesired neovascularization" refers to any disease or disorder in which neovascularization causes or contributes to damage to the eye or a particular structure of the eye (e.g., retina, macula, rods, cones, retinal pigment epithelium, Bruch's membrane, etc.) or causes or contributes to impairment of vision from the eye. Diseases and disorders contemplated by this term include but are not limited to wet AMD, diabetic retinopathy, corneal neovascularization, choroidal neovascularization, cyclitis, Hippel-Lindau Disease, retinopathy of prematurity, pterygium, histoplasmosis, iris neovascularization, macular edema, glaucoma-associated neovascularization, Purtscher's retinopathy, and the like. Although dry AMD is not primarily characterized by neovascularization, the fact that patients who develop the wet form of AMD are believed to have had the dry form of AMD first, leads us to believe that the treatments described herein will be beneficial in the treatment of dry AMD, e.g., to arrest or slow its progress, and that dry AMD may be included in this disease category.

A composition or method described herein as "comprising" one or more named elements or steps is open-ended meaning that the named elements or steps are essential, but other elements or steps may be added within the scope of the composition or method. To avoid prolixity, it is also understood that any composition or method described as "comprising" (or "comprises") one or more named elements or steps also describes the corresponding, more limited, composition or method "consisting essentially of" (or "consists essentially of") the same named elements or steps, meaning that the composition or method includes the named essential elements or steps and may also include additional elements or steps that do not materially affect the basic and novel characteristic(s) of the composition or method. It is also understood that any composition or method described herein as "comprising" or "consisting essentially of" one or more named elements or steps also describes the corresponding, more limited, and close-ended composition or method "consisting of" (or "consists of") the named elements or steps to the exclusion of any other unnamed element or step. In any composition or method disclosed herein, known or disclosed equivalents of any named essential element or step may be substituted for that element or step.

The definitions of other terms used herein are those understood and used by persons skilled in the art and/or will be evident to persons skilled in the art from their usage in the text.

The method of this invention can be practiced by using any complement inhibitory protein which is effective to block complement activation. Such complement inhibitory proteins include, for example, complement receptor type I (CR1), factor H, C4-binding protein (C4-BP), membrane cofactor protein (MCP), decay accelerating factor (DAF), or fragments thereof that retain complement inhibiting properties, such as the ability to inhibit complement activation, to bind C3b, to bind C4b, or to bind both C3b and C4b. Preferably, the complement inhibitory protein used in the methods described herein is a soluble (non-membrane-bound) form of human CR1. Suitable soluble CR1 polypeptides and preparations are described in detail, e.g., in U.S. Pat. No. 5,981,481; U.S. Pat. No. 5,456,909; and U.S. Pat. No. 6,193,979.

As discussed more fully below, it has been demonstrated herein that administration of sCR1 alleviates the effects of undesirable neovascularization, specifically in a model commonly used to assess agents useful in treating age-related macular degeneration. We have thus discovered that administration of a complement inhibitory protein to a subject in a relevant AMD model reduces and/or ameliorates the pathogenesis of new choroidal blood vessel formation believed to be caused or supported by complement activation.

In a specific embodiment, the invention relates to soluble CR1 polypeptides and their use for the treatment of AMD.

The human C3b/C4b receptor, termed complement receptor type I (CR1) or CD35, is naturally present on the membranes of erythrocytes, monocytes/macrophages, granulocytes, B cells, some T cells, splenic follicular dendritic cells, and glomerular podocytes. (Fearon, 1980, *J. Exp. Med.*, 152: 20, Wilson, J. G., et al., 1983, *J. Immunol.*, 131: 684). CR1 specifically binds C3b, C4b, and iC3b.

CR1 can inhibit the classical and alternative pathway C3/C5 convertases and act as a cofactor for the cleavage of C3b and C4b by factor I, indicating that CR1 also has complement regulatory functions in addition to serving as a receptor. (Fearon, D. T., 1979, *Proc. Natl. Acad. Sci. U.S.A.*, 76: 5867; Iida, K. I. and Nussenzweig, V., 1981, *J. Exp. Med.*, 153: 1138.) In the alternative pathway of complement activation, the bimolecular complex C3b-Bb is a C3 protease (convertase). CR1 can bind to C3b thereby promoting the dissociation of fragment Bb from the complex. In the alternative pathway of complement activation, the tri-molecular complex C3b-C3b-Bb is a C5 protease (convertase). CR1 can bind to C3b-C3b thereby promoting the dissociation of fragment Bb from the complex. Furthermore, binding of C3b to CR1 renders C3b susceptible to irreversible proteolytic inactivation by factor I, resulting in the production of inactivated derivatives of C3b (namely, iC3b, C3d and C3dg). In the classical pathway of complement activation, the bimolecular complex C4bC2a is the C3 convertase. CR1 binds to C4b thereby promoting the dissociation of C2a from the complex. In the classical pathway of complement activation, the complex C3bC4bC2a is the C5 convertase. CR1 binds to C4b and/or C3b thereby promoting the dissociation of C2a from the complex. The binding renders C4b and/or C3b susceptible to irreversible proteolytic inactivation by factor I. Finally, the lectin pathway (also called the mannose binding lectin or MBL pathway) feeds into the classical pathway upstream of the C3 convertase. Thus, CR1 inhibits lectin pathway activation through its inhibitory activities on the classical pathway at the C3 and C5 activation steps.

Factor H has some of the same properties exhibited by CR1 but is not effective to block both activation pathways. Factor H has decay accelerating activity and Factor I cofactor activity in the alternative pathway only. In addition, the activity of Factor H is restricted to non-activating surfaces. This is an important distinction with respect to CR1, which is active both on activating and non-activating surfaces and is therefore more suitable for use under conditions of an ongoing disease. Activating surfaces would include, e.g., the presence of drusen as well as necrotic and inflamed tissue.

Several soluble (non-membrane bound) fragments of CR1 have been generated via recombinant DNA procedures by eliminating the transmembrane and cytoplasmic regions from the DNAs being expressed. See, e.g., Fearon et al., Intl. Patent Publn. WO 89/09220, Oct. 5, 1989. The soluble CR1 fragments are functionally active, i.e., retaining the ability to bind C3b and/or C4b, inhibiting complement activation, and demonstrating factor I cofactor activity, depending upon the native CR1 regions the CR1 fragments contain. Such constructs inhibit in vitro the consequences of complement activation such as neutrophil oxidative burst, complement mediated hemolysis, C3a and C5a production, and the production of C5b-9 (MAC). A soluble construct, sCR1/pBSCR1c, also has demonstrated in vivo activity in a reversed passive Arthus reaction (Yeh et al., 1991, *J. Immuno.*, 146:250), suppressed post-ischemic myocardial inflammation and necrosis (Weisman et al., 1990, *Science*, 249: 146-151) and extended survival rates following transplantation (Pruitt et al., 1991, *J. Surg. Res.*, 50: 350; Pruitt et al., 1991, *Transplantation*, 52: 868).

The complete cDNA coding sequence and amino acid sequence of the human CR1 protein is described in U.S. Pat. No. 5,981,481, which is incorporated herein by reference. The isolation of the full-length CR1 gene, expression and purification of the full-length protein and active fragments thereof, and demonstration of activity in the full-length protein and fragments derived from the full-length protein, are described in U.S. Pat. No. 5,981,481. The complete cDNA coding sequence of the human CR1 protein is shown in SEQ ID NO:1. The amino acid sequence of mature human CR1 is shown in SEQ ID NO:2.

The complement inhibitory proteins such as sCR1 that are useful in the methods of the present invention are advantageously produced in quantity using recombinant DNA technology to express the protein in a host cell, such as bacterial cells, mammalian cells, or even plant cells. For the complement inhibitory proteins contemplated herein, mammalian host cells, such as Chinese Hamster ovary (CHO) cells, African Green Monkey kidney (COS) cells, or human cells, retina-derived cells (e.g., PER.C6 cells) being preferred. Yeast expression, E. coli expression, baculovirus expression, and plant expression are specifically contemplated, as it is believed that non-mammalian glycosylation patterns will not have a significant impact on biological function or pharmacokinetics in the eye. Other expression systems for the production of recombinant proteins will also be useful for the production of complement inhibitory proteins contemplated herein. The isolated gene encoding the desired protein can be inserted into an appropriate cloning vector. A large number of vector-host systems known in the art may be used. Possible vectors include, but are not limited to, plasmids or modified viruses. The vector system must be compatible with the host cell used. Such vectors include, but are not limited to, bacteriophages such as lambda derivatives, or plasmids such as pBR322, pUC or CDM8 plasmids (Seed, 1987, Nature, 329: 840-842) or derivatives of those well-known vectors. Recombinant molecules can be introduced into host cells via transformation, transfection, infection, electroporation, etc.

Recombinant cells producing a preferred form of sCR1 are deposited with the American Type Culture Collection, Rockville, Md. (accession no. CRL 10052). The deposited cells are a Chinese Hamster ovary cell line DUX B11 carrying plasmid pBSCR1c/pTCSgpt clone 35.6, encoding a soluble CR1 having the amino acid sequence of SEQ ID NO:3. Such sCR1 protein in purified form is produced under the product designation TP10 by AVANT Immunotherapeutics, Inc. (Needham, Mass.).

After expression in a host cell, the soluble CR1 molecules may be isolated and purified by standard methods including chromatography (e.g., ion exchange, affinity, and sizing column chromatography, high pressure liquid chromatography), centrifugation, differential solubility, or by any other standard technique for the purification of proteins. Preferred purification methods are described in U.S. Pat. No. 6,316,604, U.S. Pat. No. 5,252,216, and U.S. Pat. No. 5,840,858, which are incorporated herein by reference.

Soluble CR1 proteins are therapeutically useful in the modulation of complement-mediated diseases, that is, diseases or conditions characterized by inappropriate or undesired complement activation. A soluble CR1 protein or fragment which can bind C3b or C4b, and/or retain the ability to inhibit the alternative or classical C3 or C5 convertases, and/or retain factor I cofactor activity, can be used to inhibit complement activation. In the present invention, we have demonstrated that soluble CR1 can be used to ameliorate or inhibit undesirable complement activity in the pathogenesis of new choroidal blood vessel formation and macular degeneration.

In the method of the invention, a complement inhibitory protein, such as soluble CR1, is administered, preferably intravitreally, to a subject who suffers from a disease of the eye characterized by undesired neovascularization in order to attenuate complement activation and its role in the pathogenesis of new choroidal blood vessel formation and macular degeneration.

In a method of treating AMD according to the invention, a therapeutically active amount of a complement inhibitory protein or preparation thereof is administered to a mammalian subject in need of such treatment. The preferred subject is a human. The amount administered should be sufficient to inhibit complement activation or inhibit the pathogenesis of new choroidal blood vessel formation and macular degeneration. The determination of a therapeutically effective dose is within the capability of practitioners in this art, however, as an example, in embodiments of the method described herein utilizing systemic administration of sCR1 for the treatment of AMD, an effective human dose will be in the range of 0.01-100 mg/kg; preferably 0.1-10 mg/kg, most preferably 1-10 mg/kg patient body weight, depending on the route of administration. For embodiments of the method described herein utilizing local, intraocular administration of sCR1 for the treatment of AMD, an effective human dose will be in the range of 5-10,000 µg/eye, preferably 50-5,000 µg/eye, most preferably 100-1000 µg/eye. Repeated systemic and/or intraocular doses are contemplated in order to maintain an effective level, e.g., to attenuate or inhibit complement activation, in a patient's system or within the patient's eye(s), depending on the mode of administration adopted. For intraocular administration, the volume of the dosage will be a factor, since the intraocular space is limited and extremely sensitive to pressure.

Soluble CR1 or other complement inhibitory proteins may be used in combination or alternating with the administration of other therapeutics prescribed for treatment of ocular disorders involving abnormal neovascularization, especially those therapeutics having different mechanisms of action, such as anti-angiogenic agents.

For administration, the sCR1 or other therapeutic protein may be formulated into an appropriate pharmaceutical composition. Such a composition typically contains a therapeutically active amount of the sCR1 or other protein and a pharmaceutically acceptable excipient or carrier such as saline, buffered saline, salt solutions (e.g., BSS®), phosphate buffers, dextrose, or sterile water. Compositions may also comprise specific stabilizing agents such as sugars, including mannose and mannitol.

Various delivery systems are known and can be used for delivery of complement inhibitory proteins such as sCR1 polypeptides in accordance with this invention, e.g., encapsulation in liposomes, microparticles, or microcapsules. Suitable modes of administration include but are not limited to, intravitreal (intravitreous), intraocular, intradermal, intramuscular, intraperitoneal, intravenous, subcutaneous, intrathecal, or epidural injection, and oral or pulmonary delivery. A syringe such as a tuberculin syringe (i.e., a small gauge needle on a syringe designed to deliver a small volume accurately, with a low amount of "dead space") is preferred for intravitreal administration.

Pharmaceutical compositions containing one or more complement inhibitory proteins for use in the present invention may be formulated in accordance with routine procedures as a pharmaceutical composition for systemic administration to an individual suffering from macular degeneration or any related disorder of the eye. Typically compositions for systemic administration are solutions in sterile aqueous buffer. Where necessary, the composition may also include a solubilizing agent and a local anesthetic such as lidocaine to ease pain at the site of injection. Generally, the ingredients will be supplied either separately or mixed together in unit dosage form, for example, as a dry lyophilized powder or water free concentrate in a hermetically sealed container such as an ampoule or sachette indicating the quantity of active agent in activity units. Where the composition is to be administered by injection, an ampoule of sterile water for injection or saline may be provided so that the ingredients may be mixed prior to administration.

A pharmaceutical pack comprising one or more containers filled with one or more of the ingredients of the pharmaceutical composition is also contemplated.

The following examples illustrate the methods of the present invention. They are provided by way of illustration and not for purposes of limitation.

Example 1

A soluble CR1 comprising the entire extracellular domain of mature human CR1, obtained under the product designation TP10 from AVANT Immunotherapeutics, Inc. (Needham, Mass.), was used as the test composition in a concentration of 8.3 mg/ml of TP10 in BSS®. Sterile balanced salt solution (BSS®) was used as a control. BSS® is a sterile physiologically balanced; salt solution, each mL containing sodium chloride (NaCl) 0.64%, potassium chloride (KCl) 0.075%, calcium chloride dihydrate ($CaCl_2.2H_2O$) 0.048%, magnesium chloride hexahydrate ($MgCl.6H_2O$) 0.03%, sodium acetate trihydrate ($CH_3CO_2Na.3H_2O$) 0.39%, sodium citrate dihydrate ($C_6H_5O_7Na_3.2H_2O$) 0.17%, sodium hydroxide and/or hydrochloric acid (to adjust pH) and water for injection. Alcon Laboratories (Fort Worth, Tex.) supplies a comprehensive range of ophthalmic surgical pharmaceutical products, including viscoelastic solutions and intraocular irrigating solutions including BSS®.

The efficacy and safety of intravitreal administration of sCR1 following laser-induced choroidal neovascularization (CNV) was determined as follows. The mice were collected into two groups of six mice each, control (BSS®) and test (sCR1).

Male C57B16J mice of approximately 25 g were used. For all laser and examination procedures, animals were sedated with Avertin® tribromoethanol solution (Winthrop Laboratories) of 0.02 ml/gm body weight (1.25% w/v tribromoethanol, 0.8% v/v amyl alcohol). Topical 1% tropicamide and 2.5% phenylephrine were administered for pupillary dilation. A cover slip was applied to flatten the cornea, as needed.

The animals were positioned on a Mayo stand before a slit-lamp (Carl Zeiss Meditec, Jena, Germany). The fundus was visualized using a panfundus corneal contact lens and goniosol. A red-diode laser delivery system (OcuLight GL, Iris Medical Instrument, Inc., Mountain View, Calif.) was used for photocoagulation (532 nm wavelength, 0.05 second duration, 75 µm spot size, and 120 mW power) (Lambert et al., 2003, *Faseb. J.*, 17(15):2290-2292; To be et al., 1998, *Am. J. Pathol.*, 153(5):1641-1646.). To produce an acute vapor bubble suggestive of Brush's membrane rupture, a 75 µM diameter spot at a moderate laser power of 120 mW was used. A series of four photocoagulation sites were concentrically placed at equal distances (~75 to 100 µm) around the optic disk in each eye.

Within a few minutes after lasering, each animal (n=6 per group) received a 10 µl intravitreal injection in each of its eyes of either the test compound (in the sCR1 group) or BSS® (in the control group). Both eyes of each animal received the same injection.

Two weeks after laser photocoagulation, neovascular development was photographically documented by color fundus photography (Kowa Genesis fundus camera) and fluorescein angiography (FA). For FA evaluations, 25% sodium fluorescein (0.1 mg/kg) was administered intraperitoneally. The size of the laser photocoagulation sites as well as the presence of subretinal vessels, subretinal hemorrhage, subretinal fluid or subretinal lipid was noted and recorded. Individual lesion sites, photographed during late phase fluorescein angiography, were subjected to analysis for the presence and intensity of staining and leakage using the murine FA leakage score (0 "no leakage" to 3 "strong leakage") as reported previously by others (Takahashi et al., 1998, *Am. J. Opthalmol.*, 126(6):791-797).

At the conclusion of the experiment, two weeks after the laser, the animals were euthanized and the eyes enucleated and processed for histological analysis. Serial, radial tissue sections from each recovered lesion site were evaluated in their entirety to quantify the extent of fibrovascular proliferation. Histological findings from different groups were examined and compared to assess: (1) the presence or absence of neovascularization; (2) the degree of neovascularization with respect to the choroid, Bruch's membrane, and the retina; (3) the responses of the retinal pigment epithelium cells to the original injury and subsequent neovascularization; and (4) the inflammatory response to the original injury and subsequent formation of choroid neovascular membranes (CNVM).

For statistical analyses, maximum CNVM thickness measurement, which typically occurred at or near the center of the initial trauma site, was obtained from digital photographs (Nikon CoolPix 990 modified camera system) and then converted to µm measurements (using graticule image measurements for comparison). This technique demonstrated reproducibility of measurements within ±2 µm using a random sampling of representative masked lesions. Mean CNVM thickness values for each group were obtained using the maximum thickness measurements of the 4 recovered CNVM lesion sites per eye to then determine an average value for each site within each group.

The analysis for the presence and intensity of staining and leakage using the murine FA leakage score are presented in Table 1, with data represented in scale from 0 "no leakage" to 3 "strong leakage".

TABLE 1

| Marine FA Leakage Score | |
|---|---|
| BSS group score | 1.71 |
| sCR1 group score | 1.35 | p = 0.058

The data obtained from the measurement of the maximum choroid neovascular membranes (CNVM) area and thickness are presented in Table 2.

TABLE 2

| | | sCR1 group | BSS control | t-test |
|---|---|---|---|---|
| Maximum area ($µm^2$) | per laser site | 8716 ± 3507 | 11,232 ± 4359 | p = 0.018 |
| | per eye | 8744 ± 2195 | 11,213 ± 1763 | p = 0.026 |
| Maximum thickness (µm) | per laser site | 55.6 ± 16.6 | 57.6 ± 14.0 | p = 0.616 |
| | per eye | 55.5 ± 7.0 | 57.8 ± 8.2 | p = 0.549 |

The results indicate that sCR1 had a pronounced effect in reducing the choroidal neovascularization in this animal model of AMD. This is important data tending to show that inhibition of complement activation is a valid approach to the treatment of AMD and other diseases and disorders of the eye characterized by undesired neovascularization. Following the foregoing example, additional therapeutic formulations containing a complement regulatory protein such as sCR1, Factor H, C4-BP, DAF, and MCP may readily be tested, prepared and used for the treatment of AMD and related diseases of the eye characterized by undesired neovascularization.

Example 2

A soluble CR1 (sCR1) comprising the entire extracellular domain of mature human CR1, obtained under the designation TP10 from AVANT Immunotherapeutics, Inc. (Needham, Mass.), was used as the test composition in a concentration of 9.1 mg/ml of TP10 in BSS® prepared from lyophilized TP10. BSS®, commercially available from Alcon Laboratories (Fort Worth, Tex.), is a sterile physiologically balanced, salt solution, each mL containing sodium chloride (NaCl) 0.64%, potassium chloride (KCl) 0.075%, calcium chloride dihydrate ($CaCl_2.2H_2O$) 0.048%, magnesium chloride hexahydrate ($MgCl_2.6H_2O$) 0.03%, sodium acetate trihydrate ($CH_3CO_2Na.3H_2O$) 0.39%, sodium citrate dihydrate ($C_6H_5O_7Na_3.2H_2O$) 0.17%, sodium hydroxide and/or hydrochloric acid (to adjust pH) and water for injection.

BSS® was used as a negative control.

Triamcinolone acetonide was used as a positive control. Triamcinolone acetonide, USP, is a glucocorticosteroid with a molecular weight of 434.5, the chemical designation 9-Fluoro-11β,16α,17,21-tetrahydroxypregna-1,4-diene-3, 20-dione cyclic 16,17-acetal with acetone ($C_{24}H_{31}FO_6$), and the following chemical structure:

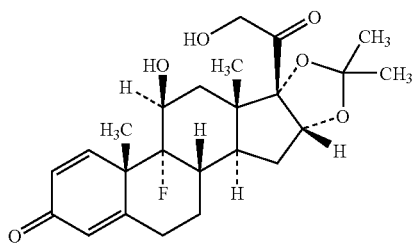

Triamcinolone acetonide is commercially available, e.g., from Bristol-Myers Squibb (Kenacort-A; New York). Triamcinolone acetonide has been used in the treatment of a variety of ocular disorders including AMD, although with the potential for complications such as transient increase in ocular pressure, cataract progression, and endophthalmitis. Özkiris et al., 2005, *Can. J. Opthalmol.*, 40:63-68.

Brown Norway rats (*Rattus norvegicus*) strain BN/Ss-NHsd, (approx. 120-200 grams; approx. 6-8 weeks of age), were obtained from Harlan Sprague Dawley, Inc. (Indianapolis, Ind.).

The efficacy and safety of both intraocular (IO) administration of sCR1 prior to laser-induced choroidal neovascularization (CNV) and intraperitoneal (IP) administration of sCR1 prior to and after laser-induced CNV was determined as follows. The rats were collected into the groups shown in Table 3.

TABLE 3

Summary of Study Design

| Group | Number of Animals | Treatment | Route | Dose | Dosing |
|---|---|---|---|---|---|
| 1 | 7 | BSS ® | IO | 10 µL/eye | Day 0 |
| 2 | 12 | sCR1 in buffered mannitol | IP | 15 mg/kg/d | Days 0, 1, 2, 3, 4 |
| 3 | 10 | sCR1 (9.1 mg/ml sCR1 in BSS ®) | IO | 10 µL/eye | Day 0 |
| 4 | 13 | Triamcinolone acetonide (40 mg/ml in BSS ®) | IO | 20 µL (0.8)/ eye | Day 0 |
| 5 | 2 | none | NA | NA | NA |

The rats were grouped into four groups of 7-13 male rats each. Two additional rats were lased, but not treated (Group 5). On Day 0, the rats of Group 3 were dosed intraocularly (IO) by injection into the vitreous of both eyes of 10 µL/eye of 9.1 mg/ml sCR1 in BSS®. The rats of the positive control group (Group 4) were also dosed intraocularly by injection into the vitreous of both eyes with 20 µL/eye of 40 mg/ml Triamcinolone acetonide in BSS®. As a negative control, the Group 1 rats were dosed intraocularly on Day 0 by injection into the vitreous of both eyes with 10 µL/eye of BSS®. Starting on Day 0, the Group 2 rats were dosed once daily for 5 days (Days 0-4) by intraperitoneal (IP) injection of 15 mg/kg/day of lyophilized sCR1 (in buffered mannitol) reconstituted in water. After the Day 0 dosing, the retinae of both eyes of each animal were lased.

For all laser procedures, animals were anesthetized briefly. Tropicamide was administered for pupillary dilation. A cover slip was applied to flatten the cornea, as needed.

The retinas were lased using a retinal lasering device (Index DioVet laser, wavelength 810 nm) with an attached Kowa PortSlit, SC14; Keeler fison Indirect Opthalmoscope (Lens 30 Diopter). To produce an acute vapor bubble suggestive of Bruch's membrane rupture, a 75 µM diameter spot at a laser power of 130 mW, 0.1 second duration was used. A series of three photocoagulation sites were placed at the nine, twelve, and three o'clock positions, 2-3 disk diameters from the optic nerve in each eye. Rupture of the Bruch's membrane was identified by bubble formation, which was observed immediately, at the site of photocoagulation.

The fundus was photographed (Kowa Small Animal Fundus Camera) at the time of lasing (before and after) and prior to necropsy. To illuminate the retinal vasculature, animals were administered sodium, fluorescein (0.1 ml of 10% fluorescein dye) intraperitoneally about 5 minutes before photography immediately following lasing and prior to necropsy.

Two weeks after lasing, the animals were deeply anesthetized with $CO_2$, injected intravenously with 0.1 ml 25% sodium fluorescein intravenously and the fundus was again photographed. The animals were euthanized and the eyes enucleated and processed for histological analysis. The left eye of each animal was collected in Davidson's Fixative (glacial acetic acid, ethyl alcohol, formaldehyde, eosin, and distilled water), and the right eye of each was collected into Davidson's solution and changed into 70% ethanol so that the eye could be prepared as a retinal whole mount to be stained for immunohistochemical stains for neovascularization.

Fixed tissues for histopathologic examination were dehydrated, embedded in paraffin, sectioned at 3-5 µm, and stained with hematoxylin and eosin. For histopathology, eyes were oriented sagitally and then sectioned from the lateral part of the eye through the retinal-optic nerve region. Digital photographs were made using a 200× objective, an Olympus 3.3 megapixel Q-Fire digital camera, and Q-Capture software (Quantitative Imaging Corp.). Perimeters and areas of the neovascular plaque at the burn site were measured using the program ImageJ 1.30v+, which is available through the National Institutes of Health. The scale (pixels/mm) was set using a stage micrometer (Graticules Ltd., Tonbridge, Kent, England) having a 1 mm scale with 100 divisions. A scale of 5.75 pixels/mm was used for the images of the retinal sections. This scale was in good agreement with previous calibration of the same equipment. In most cases, one representative section of the burn site was analyzed for each left eye. All measurements (µm) were entered by hand into an Excel® spreadsheet as the data were obtained. The mean and standard deviation of the neovascular plaque thickness were determined.

The data obtained from the measurement of the neovascular plaque thickness are illustrated in FIG. 1.

TABLE 4

| Group | Number of Animals | Treatment | No. Rats with lesions | Comments |
|---|---|---|---|---|
| 1 | 7 | 10 µl BSS ®, intraocular | 7/7 | Plaque present in all eyes |
| 2 | 12 | sCR1 in buffered mannitol at 15 mg/kg/day for 5 days, intraperitoneal | 7/12 | Plaque present in 7 of 12, 5 with no lesions observed; mean thickness of the 7 with plaques was 8.2 ± 2.9 |
| 3 | 10 | 10 µl sCR1 (9.1 mg/ml sCR1 in BSS ®), intraocular | not determined | Retinal integrity lost, could not be measured |
| 4 | 10* | 20 µl Triamcinolone acetonide (40 mg/ml in BSS ®), intraocular | 10/10 | Plaque present in all eyes |
| 5 | 2 | None (lasing only) | 2/2 | Untreated, lased rats |

*three subjects inconclusive and excluded

Group 1: Vehicle (IO). Focal areas of neovascular proliferation were present on the retinas of all animals in the group. The lesion consisted of focal thickening on the surface of the retina at the optic nerve fiber layer. The thickening was composed of proliferating new vessels. There was no associated inflammation.

Group 2: 15 mg/kg/day sCR1 (IP). Small focal areas of neovascular proliferation were present on the retinas of all animals in the group but were surprisingly less extensive or severe than those seen in Groups 1, 4 and 5. The lesion consisted of focal thickening on the surface of the retina at the optic nerve fiber layer. The thickening was composed of proliferating new vessels. There was no associated inflammation.

Group 3: 10 µL sCR1 (IO). No neovascular proliferation was discernable in this group. The outer nerve fiber layer of the retina was compromised. Accumulations of neutrophils and proteinaceous material was present in the vitreous in 5 of 12 animals. At the time of injection, it was noted that the test article (TP10 solution) was visible in the vitreous humor and did not dissipate rapidly. It is likely that the presence of the test article in the vitreous humor produced gradients in the index of refraction which caused a diffraction and dispersion of the laser beam leading to extensive damage of the retina. This effect could be avoided by lasing immediately before intravitreal injection of the test article.

Group 4: Triamcinolone (0.8 mg/eye). Focal areas of neovascular proliferation were present on the retinas of all animals in the group but were less severe than that seen in Group 1 and Group 5. The lesion consisted of focal thickening on the surface of the retina at the optic nerve fiber layer. The thickening was composed of proliferating new vessels. There was no associated inflammation.

Group 5: Untreated lasered rats. Two rats subjected to lasing, but receiving no treatment in the eye, were also examined. Focal areas of neovascular proliferation were present on the retinas of all animals in the group. The lesion consisted of focal thickening on the surface of the retina at the optic nerve fiber layer. The thickening was composed of proliferating new vessels. There was no associated inflammation.

Figure 2:
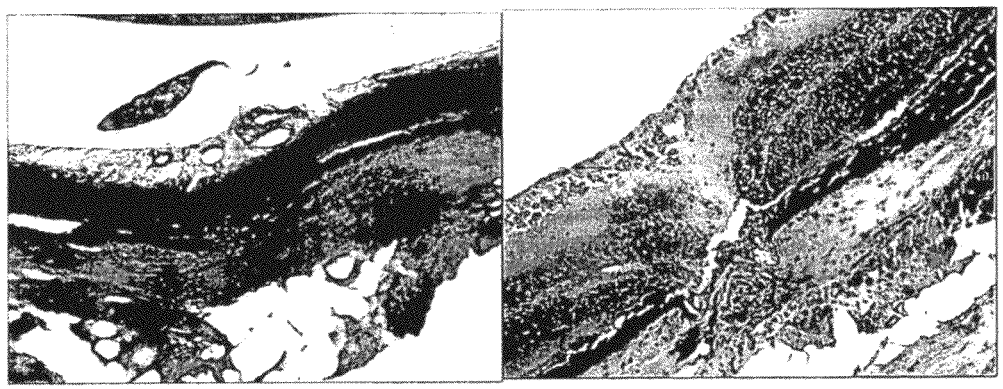
FIG. 2 shows histopathologic slides exemplifying the choroidal neovascularization in a test animal treated with sCR1 and in a vehicle-treated (negative control) subject. These slides show the characteristic lesions and choroidal neovascularization of the CNV model.
Figure 3:
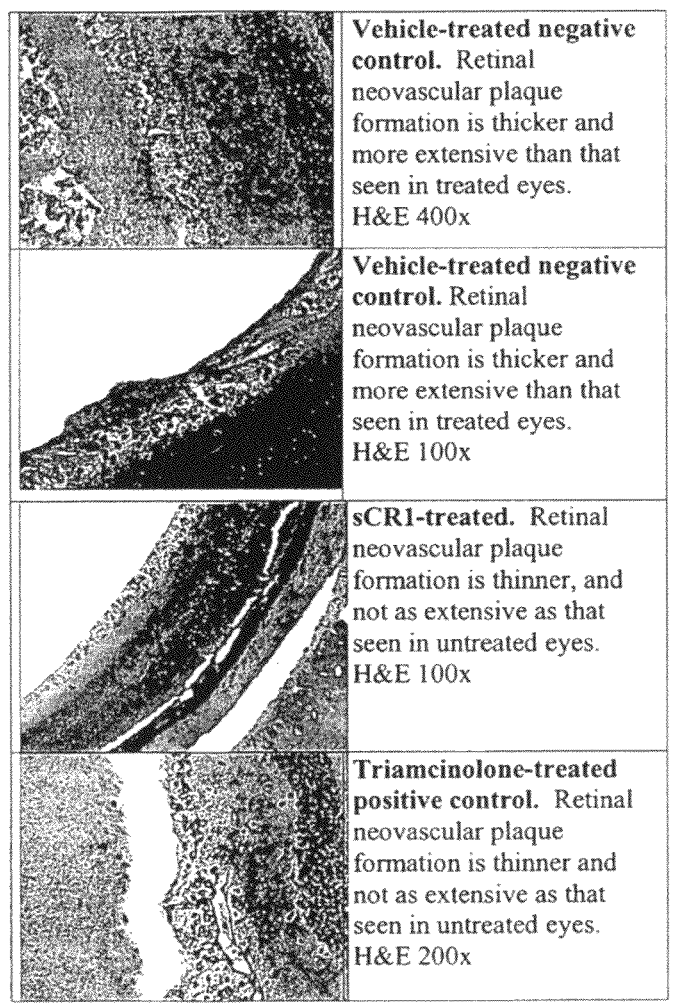
FIG. 3 are histopathologic slides comparing the retinal neovascularization in test animals treated with sCR1 vs. positive (Triamcinolone) and negative (vehicle) controls. The first panel shows results from a subject treated with vehicle only (negative control) (hematoxylin and eosin stain, magnification 400×): it is seen that retinal neovascular plaque formation is thicker and more extensive than that seen in samples from treated subjects. The second panel shows results from a subject treated with vehicle only (negative control) (hematoxylin and eosin stain, magnification 100×): it is seen that retinal neovascular plaque formation is thicker and more extensive than that seen in samples from treated subjects. The third panel shows results from a subject treated with sCR1 (hematoxylin and eosin stain, magnification 100×): it is seen that retinal neovascular plaque formation is thinner an not so extensive than that seen in samples from untreated subjects. The fourth panel shows results from a subject treated with Triamcinolone (hematoxylin and eosin stain, magnification 200×): it is seen that retinal neovascular plaque formation is thinner an not so extensive than that seen in samples from untreated subjects.

The results indicate that a focal neovascular lesion ("neovascular plaque") is reliably induced by the lasing procedure. See FIG. 2. The lesion is characterized by a focal area of vascular leakage at the time of injury as indicated by the fluorescein dye and fundus photography. There is a residual lesion still present at two weeks. As shown in FIG. 3, examination of the retina by histopathologic examination by light microscopy indicates that both Triamcinolone administration intraocularly, and sCR1 administration intraperitoneally for 5 days, results in pronounced reduction in the thickness of the neovascular plaque formation, indicating a positive therapeutic effect for both agents in this animal model of AMD. This is important data tending to show that inhibition of complement activation is a valid approach to the treatment of AMD and other diseases and disorders of the eye characterized by undesired neovascularization.

Intravitreal administration of sCR1 appeared to be associated with damage and loss to the optic nerve fiber layer of all treated animals, with additional associated mild inflammation of the vitreous. It is not believed that the dose of sCR1 was injurious to the retina. Rather, since the sCR1 was administered prior to lasing, the refractive properties of the sCR1 solution led to dispersion of the laser beam and general internal damage to the eye. In view of the pronounced positive effect found with the systemic administration of sCR1, it is believed that intravitreal administration following the lasing procedure will produce a similarly positive therapeutic effect.

Following the foregoing description, additional therapeutic formulations containing a complement regulatory protein such as sCR1, Factor H, C4-BP, DAF, and MCP may readily be tested, prepared and used for the treatment of AMD and related diseases of the eye characterized by undesired neovascularization. Additional embodiments of the invention and alternative methods adapted to a particular composition and mode of delivery will be evident from studying the foregoing description. All such embodiments and obvious alternatives are intended to be within the scope of this invention, as defined by the claims that follow.

Publications referred to above are hereby incorporated by reference.

What is claimed is:

1. A method for treating a disease of the eye characterized by undesired neovascularization in a mammalian subject comprising administering to a mammalian subject in need of treatment an effective amount of a complement inhibitory protein comprising a soluble complement receptor type I.

2. The method according to claim 1, wherein said complement inhibitory protein is administered by an intraocular route.

3. The method according to claim 2, wherein said intraocular administration is intravitreal administration.

4. The method according to claim 1, wherein said complement inhibitory protein is administered by a intradermal, intramuscular, intraperitoneal, intravenous, subcutaneous, intrathecal, epidural, oral or pulmonary route.

5. The method of claim 1, wherein said disease of the eye is age-related macular degeneration (AMD), diabetic retinopathy, corneal neovascularization, choroidal neovascularization, cyclitis, Hippel-Lindau Disease, retinopathy of prematurity, pterygium, histoplasmosis, iris neovascularization, macular edema, glaucoma-associated neovascularization, and Purtscher's retinopathy.

6. The method of claim 5, wherein said disease of the eye is wet AMD.

7. The method of claim 5, wherein said disease of the eye is dry AMD.

8. The method of claim 1, wherein said soluble complement receptor type I is selected from the group consisting of: a soluble CR1 polypeptide having glycosylation modified to exhibit sialyl Lewis X moieties (sCR1-sLe$^x$), a soluble construct having two CR1 polypeptide moieties linked to an immunoglobulin Fc region (sCR1-F(ab)$_2$ fusion), a soluble CR1 polypeptide comprising the extracellular domain of mature human CR1 (SEQ ID NO:3), and a soluble CR1 polypeptide as expressed by Chinese hamster ovary DUX B11 cells as deposited under ATCC accession no. CRL 10052.

9. The method of claim 1, wherein said soluble complement receptor type I is a soluble CR1 polypeptide comprising the extracellular domain of mature human CR1 (SEQ ID NO:3).

10. The method of claim 5, wherein said subject is a human, said soluble complement receptor type I is a soluble CR1 polypeptide comprising the extracellular domain of mature human CR1 (SEQ ID NO:3), said disease of the eye is age-related macular degeneration (AMD), and said administering is systemic administration.

11. The method of claim 10, wherein said human subject is administered an amount of soluble complement receptor type I of 0.1-10 mg/kg body weight.

12. The method of claim 5, wherein said subject is a human, said soluble complement receptor type I is a soluble CR1 polypeptide comprising the extracellular domain of mature human CR1 (SEQ ID NO:3), said disease of the eye is age-related macular degeneration (AMD), and said administering is intraocular.

13. The method of claim 12, wherein said human subject is administered an amount of soluble complement receptor type I of 5-10,000 µg/eye.

* * * * *